US008815831B2

(12) United States Patent
Onsoyen et al.

(10) Patent No.: US 8,815,831 B2
(45) Date of Patent: *Aug. 26, 2014

(54) TREATMENT OF ACINETOBACTER WITH ALGINATE OLIGOMERS AND ANTIBIOTICS

(75) Inventors: Edvar Onsoyen, Sandvika (NO); Rolf Myrvold, Sandvika (NO); Arne Dessen, Sandvika (NO); David Thomas, Cardiff (GB); Timothy Rutland Walsh, Cardiff (GB)

(73) Assignee: Algipharma AS, Sandvika (NO)

( * ) Notice: Subject to any disclaimer, the term of this patent is extended or adjusted under 35 U.S.C. 154(b) by 0 days.

This patent is subject to a terminal disclaimer.

(21) Appl. No.: 13/376,140

(22) PCT Filed: Jun. 3, 2010

(86) PCT No.: PCT/GB2010/001096
§ 371 (c)(1),
(2), (4) Date: Jan. 26, 2012

(87) PCT Pub. No.: WO2010/139956
PCT Pub. Date: Dec. 9, 2010

(65) Prior Publication Data
US 2012/0115803 A1    May 10, 2012

(30) Foreign Application Priority Data

Jun. 3, 2009  (GB) .................................. 0909557.1
Aug. 7, 2009  (GB) .................................. 0913829.8
Oct. 14, 2009  (GB) .................................. 0917995.3

(51) Int. Cl.
| | |
|---|---|
| *A61K 31/734* | (2006.01) |
| *A61K 31/715* | (2006.01) |
| *A61K 31/7048* | (2006.01) |
| *A61K 31/7042* | (2006.01) |
| *A61K 31/7036* | (2006.01) |
| *A61P 31/00* | (2006.01) |
| *A61P 31/04* | (2006.01) |

(52) U.S. Cl.
USPC .................. 514/54; 514/23; 514/61; 514/53; 514/29; 514/30; 536/123.1

(58) Field of Classification Search
USPC ............ 514/54, 23, 61, 53, 29, 30; 536/123.1
See application file for complete search history.

(56) References Cited

U.S. PATENT DOCUMENTS

| | | | |
|---|---|---|---|
| 4,225,592 | A | 9/1980 | Lakatos et al. |
| 5,166,137 | A | 11/1992 | Otterlei et al. |
| 5,169,840 | A | 12/1992 | Otterlei et al. |
| 5,192,362 | A | 3/1993 | Harvey et al. |
| 5,683,991 | A | 11/1997 | Guggenbichler et al. |
| 6,121,441 | A | 9/2000 | Simensen et al. |
| 6,339,075 | B1 | 1/2002 | King et al. |
| 6,395,307 | B1 | 5/2002 | Banning et al. |
| 6,407,226 | B1 | 6/2002 | Simensen et al. |
| 6,641,740 | B2 | 11/2003 | Cornelius et al. |
| 7,208,141 | B2 | 4/2007 | Montgomery |
| 7,671,100 | B2 | 3/2010 | Gaserod et al. |
| 7,671,101 | B2 | 3/2010 | Gaserod et al. |
| 7,671,102 | B2 | 3/2010 | Gaserod et al. |
| 7,674,837 | B2 | 3/2010 | Gaserod et al. |
| 7,758,856 | B2 | 7/2010 | Hughes et al. |
| 7,776,839 | B2 | 8/2010 | Del Buono et al. |
| 7,790,699 | B2 | 9/2010 | Melvik et al. |
| 2003/0013678 | A1 | 1/2003 | Lang et al. |
| 2003/0022863 | A1 | 1/2003 | Stahl et al. |
| 2003/0224070 | A1 | 12/2003 | Sweazy et al. |
| 2004/0073964 | A1 | 4/2004 | Ellington et al. |
| 2004/0224922 | A1 | 11/2004 | King |
| 2010/0068290 | A1 | 3/2010 | Ziegler et al. |
| 2010/0305062 | A1 | 12/2010 | Onsoyen et al. |

FOREIGN PATENT DOCUMENTS

| | | |
|---|---|---|
| DE | 268865 A1 | 1/1987 |
| EP | 0324720 A1 | 7/1989 |
| EP | 0 506 326 A2 | 9/1992 |
| EP | 0590746 A1 | 4/1994 |
| EP | 1234584 A1 | 8/2002 |
| EP | 1714660 A1 | 10/2006 |
| EP | 1745705 A1 | 1/2007 |
| FR | 7576 M | 3/1968 |
| GB | 1042379 | 9/1966 |
| GB | 2430881 A | 4/2007 |
| JP | 05-252970 | 10/1993 |

(Continued)

OTHER PUBLICATIONS

Office Action in corresponding Chinese Application No. CN 200880118093.0 dated Nov. 29, 2012.

Office Action in corresponding Chinese Application No. CN 201080034492.6 dated Oct. 24, 2012.

Office Action in corresponding Russian Application No. 2010120766 dated Sep. 26, 2012.

Office Action in related United Kingdom Patent Application No. GB1122180.1, dated Jan. 20, 2012.

Alkawash, M.A. et al. 2006 "Alginate lyase enhances antibiotic killing of mucoid *Pseudomonas aeruginosa* in biofilms" *APMIS*, 114(2):131-138.

(Continued)

*Primary Examiner* — Shaojia Anna Jiang
*Assistant Examiner* — Michael C Henry
(74) *Attorney, Agent, or Firm* — Knobbe, Martens, Olson & Bear, LLP

(57) ABSTRACT

The invention provides a method to improve the efficacy of an antibiotic to inhibit the growth of *Acinetobacter*, said method comprising using said antibiotic together with an alginate oligomer. The *Acinetobacter* may be on an animate or inanimate surface and both medical and non-medical uses and methods are provided. In one aspect the invention provides an alginate oligomer for use together with at least one antibiotic in treating a subject infected, suspected to be infected, or at risk of infection, with *Acinetobacter*. In another aspect the method can be used to combat *Acinetobacter* contamination of a site e.g., for disinfection and cleaning purposes.

37 Claims, No Drawings

(56) References Cited

FOREIGN PATENT DOCUMENTS

| JP | 09208472 | 8/1997 |
|---|---|---|
| JP | 2005145885 | 11/2003 |
| JP | 2008285431 | 5/2007 |
| KR | 20000032630 | 11/1998 |
| WO | WO 98/02488 A1 | 1/1988 |
| WO | WO 98/51710 A1 | 11/1988 |
| WO | WO 88/09794 A1 | 12/1988 |
| WO | WO 91/11205 A1 | 8/1991 |
| WO | WO 94/09124 A1 | 4/1994 |
| WO | WO 95/18145 A1 | 7/1995 |
| WO | WO 98/51342 A1 | 11/1998 |
| WO | WO 01/15672 A2 | 3/2001 |
| WO | WO 01/66084 A2 | 9/2001 |
| WO | WO 03/045402 A1 | 6/2003 |
| WO | WO 03/046199 A2 | 6/2003 |
| WO | WO 2004/011628 A1 | 2/2004 |
| WO | WO 2005/023176 A2 | 3/2005 |
| WO | WO 2005/079210 A2 | 9/2005 |
| WO | WO 2006/120705 A2 | 11/2006 |
| WO | WO 2007/039754 A1 | 4/2007 |
| WO | WO 2007/039760 A2 | 4/2007 |
| WO | WO 2008/006658 A1 | 1/2008 |
| WO | WO 2008/071407 A2 | 6/2008 |
| WO | WO 2008/082948 A2 | 7/2008 |
| WO | WO 2008/125828 A2 | 10/2008 |
| WO | WO 2009/018060 A1 | 2/2009 |
| WO | WO 2009/032433 A1 | 3/2009 |
| WO | WO 2009/068841 A2 | 6/2009 |
| WO | WO 2009068841 A2 * | 6/2009 |

OTHER PUBLICATIONS

Appleman, M.D. et al. 2000 "In vitro activities of nontraditional antimicrobials against mutiresistant *Acinetobacter baumannii* strains isolated in an intensive care unit outbreak" *Antimicrobial Agents and Chemotherapy* 44: 1035-1040.

Araque-Calderon, Y. et al. 2008 "Antibiotic resistance patterns and SDS-PAGE protein profiles of *Burkholderia cepacia* complex isolates from nosocomial and environmental sources in Venezuela" *Med Sci Monit* 14: BR49-55.

Banning, D. et al. 1997 "Oscillatory and thermorheological characterization of alginate/mucin mixes" *Pharmacy and Pharmacology*, 49(Supp. 4) Poster 65.

Cannon, C. et al. 2006 "Emerging Pulmonary Infections in Cystic Fibrosis" *US Respiratory Disease*, pp. 27-29.

Cuenca, F.F. et al. 2003 "Actividad in vitro de azitromicina frente a aislamientos clinicos de *Acinetobacter baumannii*" *Rev Esp Quimioterap* 16: 204-208.

Dizbay, M. et al. 2009 "Nosocomial *Burkholderia cepacia* infections in a Turkish university hospital: a five-year surveillance" *J Infect Dev Ctries* 3: 273-277.

Djordjevic, D. et al. 2002 "Microtiter Plate Assay for Assessment of *Listeria monocytogenes* Biofilm Formation" *Appl Environ Microbiol* 68:2950-2958.

Donlan, R. M. et al. 2002 "Biofilms: Survival Mechanisms of clinically Relevant Microorganisms" *Clin. Mic. Rev.* 15(2):167-193.

Dunne, W.M. Jr. 2002 "Bacterial Adhesion: Seen Any good Biofilms Lately?" *Clinical Microbiology Reviews*, 15(2):155-166.

Ertesvåg, H. et al. 1999 "Mannuronan C-5-Empimerases and Their Application for in Vitro and in Vivo Design of New Alginates Useful in Biotechnology" *Metabolic Engineering* 1:262-269.

Ferguson, D. et al. 2007 "Phenotypic, molecular and antibiotic resistance profiling of nosocomial *Pseudomonas aeruginosa* strains isolated from two Irish Hospitals" J Medicine vol. 1. (available online at: http://www.scientificjournals.org/journals2007/articles/1055.htm.

Flo, T. et al. 2000 "Involvement of CD14 and β2-Integrins in Activating Cells with Soluble and Particulate Lipopolysaccharides and Mannuronic Acid Polymers" *Infection and Immunity*, 68(12):6770-6776.

Fernandez-Cuenca, F. et al. 2003 "In vitro activity of Azithromycin in combination with Amikacin, Ceftazidime, Ciprofloxacin or Imipenem against clinical isolates of *Acinetobacter baumannii*" *Chemotherapy* 49: 24-26.

Gimmestad, M et al. 2003 "The *Pseudomonas fluorescens* AlgG Protein, but not its Mannuronan C-5-Epimerase Activity, is needed for Alginate Polymer Formation" *Journal of Bacteriology*, 185(12):3515-3523.

Gimmestad, M. et al. 2006 "Identification and Characterization of an *Azotobacter vinelandii* Type I Secretion System Responsible for Export of the AlgE-Type Mannuronan C-5-Epimerases" *Journal of Bacteriology*, 188(15):5551-5560.

Head, N.E. et al. 2004 "Cross-Sectional Analysis of Clinical and Environmental Isolates of *Pseudomonas aeruginosa*: Biofilm Formation, Virulence, and Genome Diversity" *Infection and Immunity* 72(1):133-144.

Jahr T.G. et al. 1997 "Induction of Tumor Necrosis Factor Production from Monocytes Stimulated with Mannuronic Acid Polymers and Involvement of Lipopolysaccharide-Binding Protein, CD14, and Bactericidal/Permeability-increasing Factor" *Infection and Immunity* 65(1):89-94.

Kitamikado, M. et al 1992 "Two Types of Bacterial Alginate Lyases" *Appl Environ Microbiol* 58(8):2474-2478.

Lasa, I. 2006 "Towards the identification of the common features of bacterial biofilm development" *International Microbiology*, 9:21-28.

McGowan, J.E. Jr. "Resistance in nonfermenting gram-negative bacteria: multidrug resistance to the maximum" *Am J Infection Control* 34: S29-S37.

Moore, J.E. et al. 2001 "Antibiotic resistance in *Burkholderia cepacia* at two regional cystic fibrosis centres in Northern Ireland: is there a need for synergy testing?" *J Antimicrobial Chemotherapy* 48: 315-329.

Moskowitz, S.M. et al. 2004 "Clinically Feasible Biofilm Susceptibility Assay for Isolates of *Pseudomonas aeruginosa* from Patients with Cystic Fibrosis" *Journal of Clinical Microbiology* 42(5): 1915-1922.

Mrsny R.J., et al. 1994 "Addition of a Bacterial Alginate Lyase to Purulent CF Sputum in Vitro Can Result in the Disruption of Alginate and Modification of Sputum Viscoelasticity" *Pulmonary Pharmacology*, 7:357-366.

Murata, K et al. 1992 "Continuous Depolymerization of Alginates by a Non-Support Bioreactor System Containing Flocculated Bacterial Cells" *Journal of Fermentation and Bioengineering* 73(2):172-174.

Otterlei, M et al. 1991 Induction fo Cytokine Production from Human Monocytes Stimulated with Alginate *Journal of Immunotherapy*, 10:286-291.

Qiu, D, et al. 2007 "Regulated proteolysis controls mucoid conversion in *Pseudomonas aeruginosa*" *Proc Natl Acad Sci USA* 104(19):8107-8112.

Remminghorst, U. et al. 2006 "Bacterial alginates: from biosynthesis to applications" *Biotechnology Letters* 28:1701-1712.

Strugala et al. 2004, "Bioactive Properties of Epimerised Alginates" *Gums and Stabilisers for the Food Industry* 12:84-94.

Tang, J. X. et al. 2005 "Anionic poly(amino acid)s dissolve F-actin and DNA bundles, enhance DNase activity, and reduce the viscosity of cystic fibrosis sputum" *American Journal of Physiology—Lung, Cellular and Molecular Physiology* 289: L599-L605.

Thibault, F.M. et al. 2004 "Antibiotic susceptibility of 65 isolates of *Burkholderia pseudomallei* and *Burkholderia mallei* to 35 antimicrobial agents" *J Antimicrobial Chemotherapy* 54: 13134-1138.

Ying, Q-L et al. 1996 "Alginate, the Slime Exopolysaccharide of *Pseudomonas aeruginosa*, Binds Human Leukocyte Elastase, Retards Inhibition by α-Proteinase Inhibitor, and Accelerates Inhibition by Secretory Leukoprotease Inhibitor" *American Journal of Respiratory Cell and Molecular Biology*, 15:283-291.

Yu, H. et al. 2002 "Persistent Infections and Immunity in Cystic Fibrosis" *Frontiers in Bioscience* 7:d442-457.

Office Action in corresponding United Kingdom Application No. GB1122180.1, dated Jul. 10, 2012.

Kitamikado, M. et al. 1993 "Bacteriostatic Action of Oligosaccharides Prepared from Alginate by Enzymatic Degradation" *Nippon Suisan Gakkaishi—Bulletin of the Japanese Society of Scientific Fisheries* 59: 315-320.

(56) References Cited

OTHER PUBLICATIONS

Hu, X. et al. 2005 "Antibacterial activity of lyase-depolymerized products of alginate" *Journal of Applied Phycology* 17: 57-60.

Office Action in related European Patent Application No. 08 875 658.0-2103, dated Jun. 19, 2012.

Office Action in corresponding Chinese Patent Application No. 201080034364.1, dated Jan. 14, 2013.

Office Action in corresponding United Kingdom Patent Application No. GB1122180.1, dated Mar. 7, 2013.

Emanuel, C. et al. 2012 "OligoG, a Novel Antimicrobial Alginate Oligosaccharide, Impedes Biofilm Development by Inhibition of Bacterial Motility" Poster No. F-2062 at IACC, San Francisco, Sep. 9-12, 2012.

Khan S. et al. 2010 "Synergistic Activity of OligoG with Anti-Gram-Negative Antibiotics against *Pseudomonas aeruginosa* and *Burkholderia spp.*" Poster No. F1-1601 at ICAAC, Boston, Sep. 12-15, 2010.

Khan S. et al. 2010 "Effect of OligoG on Disruption of *Acinetobacter baumannii* Biofilms and Overcoming Multi-Drug Resistance" Poster No. F1-1602 at ICAAC, Boston, Sep. 12-15, 2010.

Khan S. et al. 2010 "Activity of OligoG Alginate Against Gram-Positive Bacteria, Alone and in Combination with Anti-Gram Positive Antibiotics" Poster No. F1-1600 at ICAAC, Boston, Sep. 12-15, 2010.

Khan, S. et al. 2011 "The Antimicrobial Effect of Alginate Oligosaccharides for the Treatment of Multi-Drug Resistant Bacterial Infections may be due to Cell Wall Disruption?" Poster No. F1-154 at ICAAC, Chicago, Sep. 17-20, 2011.

Powell, L. et al. 2012 "The Effects of the Alginate Oligosaccharide Oligo-G on the Surface and Rheological Properties of Gram-Negative Bacterial Biofilms using Atomic Force Microscopy" Poster at European Cystic Fibrosis Conference, Jun. 11, 2012.

Sletta, H. et al. 2011 "The Ability of Novel Alginate Oligosaccharides to Impair Fungal Adherence, Biofilm Formation and Potentiate Conventional Anti-Fungal Therapy in vitro" Poster No. F1-155 at ICAA, Chicago, Sep. 17-20, 2011.

* cited by examiner

TREATMENT OF ACINETOBACTER WITH ALGINATE OLIGOMERS AND ANTIBIOTICS

The present invention relates to the use of alginate oligomers to potentiate or to improve the efficacy of an antibiotic, e.g. a macrolide antibiotic, against *Acinetobacter* organisms and in particular the effectiveness (or efficacy) of an antibiotic, e.g. macrolide antibiotic, to inhibit the growth of *Acinetobacter* organisms. The invention is based on an observation of synergy between alginate oligomers and antibiotics against *Acinetobacter*, and accordingly provides alginate oligomers for use together with (or in combination or conjunction with) an antibiotic, e.g. a macrolide antibiotic, for combating *Acinetobacter* contamination (i.e. colonisation) of a location, combating a population of *Acinetobacter* organisms and, in particular, the treatment of an *Acinetobacter* infection in a subject.

*Acinetobacter* is a genus of bacteria that are strictly aerobic non-fermentative gram-negative bacilli. *Acinetobacter* species are widely distributed in nature and can survive for long periods of time on wet or dry surfaces. *Acinetobacter* species are considered to be non-pathogenic to healthy subjects, but it is becoming increasingly apparent that *Acinetobacter* species persist in hospital environments for a long period of time and can be responsible for nosocomial infections in compromised patients. *Acinetobacter baumannii* is a frequent cause of nosocomial pneumonia, especially of late-onset ventilator associated-pneumonia and it can cause various other infections including skin and wound infections, bacteraemia, and meningitis. *Acinetobacter Iwoffii* has also been associated with meningitis. Other species including *Acinetobacter haemolyticus, Acinetobacter johnsonii, Acinetobacter junii, Acinetobacter radioresistens, Acinetobacter tandoii, Acinetobacter tjernbergiae, Acinetobacter towneri*, or *Acinetobacter ursingii* have also been linked to infection. Of particular note is the prevalence of *Acinetobacter baumannii* infections in US serviceman stationed in the Middle East, e.g. Iraq.

Of concern is the fact that many *Acinetobacter* strains appear to be multidrug resistant, thus making the combat of *Acinetobacter* infections and contamination difficult. Multidrug resistance (MDR) in bacteria describes the situation where a bacterium is resistant to at least three classes of drugs, specifically in the context of bacteria, at least three classes of anti-microbial (or more specifically anti-bacterial) agents, and particularly in the context of the present invention, at least three classes of antibiotics. Antibiotics in one class are functionally unrelated, structurally unrelated, or both, to antibiotics in a different class. MDR in bacteria is thus often termed multiple anti-bacterial drug resistance or multiple antibiotic resistance. The terms are used interchangeably in the art and herein. Bacteria displaying multidrug resistance phenotypes (or multiple antibacterial/antibiotic drug resistance phenotypes) are referred to as MDR bacteria (or sometimes MAR bacteria). Again, these terms are used interchangeably in the art and herein.

However, *Acinetobacter* infections may cause a problem even if the organism is not MDR. As such, there is an urgent need for safe and effective treatments for *Acinetobacter* infections and contamination, including those of MDR *Acinetobacter*.

Alginates are linear polymers of (1-4) linked β-D-mannuronic acid (M) and/or its C-5 epimer α-L-guluronic acid (G). The primary structure of alginates can vary greatly. The M and G residues can be organised as homopolymeric blocks of contiguous M or G residues, as blocks of alternating M and G residues and single M or G residues can be found interspacing these block structures. An alginate molecule can comprise some or all of these structures and such structures might not be uniformly distributed throughout the polymer. In the extreme, there exists a homopolymer of guluronic acid (polyguluronate) or a homopolymer of mannuronic acid (polymannuronate).

Alginates have been isolated from marine brown algae (e.g. certain species of *Durvillea, Lessonia* and *Laminaria*) and bacteria such as *Pseudomonas aeruginosa* and *Azotobacter vinelandii*. Other pseudomonads (e.g. *Pseudomonas fluorescens, Pseudomonas putida*, and *Pseudomonas mendocina*) retain the genetic capacity to produce alginates but in the wild they do not produce detectable levels of alginate. By mutation these non-producing pseudomonads can be induced to produce stably large quantities of alginate.

Alginate is synthesised as polymannuronate and G residues are formed by the action of epimerases (specifically C-5 epimerases) on the M residues in the polymer. In the case of alginates extracted from algae, the G residues are predominantly organised as G blocks because the enzymes involved in alginate biosynthesis in algae preferentially introduce the G neighbouring another G, thus converting stretches of M residues into G-blocks. Elucidation of these biosynthetic systems has allowed the production of alginates with specific primary structures (WO 94/09124, Gimmestad, M et al, Journal of Bacteriology, 2003, Vol 185 (12) 3515-3523 and WO 2004/011628).

Alginates are typically isolated from natural sources as large high molecular weight polymers (e.g. an average molecular weight in the range 300,000 to 500,000 Daltons). It is known, however, that such large alginate polymers may be degraded, or broken down, e.g. by chemical or enzymatic hydrolysis to produce alginate structures of lower molecular weight. Alginates that are used industrially typically have an average molecular weight in the range of 100,000 to 300,000 Daltons (such alginates are still considered to be large polymers) although alginates of an average molecular weight of approximately 35,000 Daltons have been used in pharmaceuticals.

It has now been found that alginate oligomers can greatly enhance the effect of antibiotics, including particularly macrolide antibiotics, but also antibiotics in other classes, against *Acinetobacter* organisms and so the use of alginate oligomers together with antibiotics, e.g. macrolide antibiotics, constitutes a highly effective treatment of *Acinetobacter* contamination and infections. Alginate oligomers appear to be particularly effective in potentiating, or enhancing, the effect of antibiotics against bacteria of the genus *Acinetobacter*. In other words, in the case of this particular bacterial genus, alginate oligomers appear to demonstrate a surprising synergistic action with antibiotics. The effect of potentiating, or enhancing, antibiotic action is particularly pronounced for this genus.

Accordingly, in a first aspect the invention provides a method to improve the efficacy of an antibiotic, e.g. a macrolide antibiotic, and in particular the effectiveness or efficacy) of an antibiotic, e.g. a macrolide antibiotic, to inhibit the growth and/or viability of *Acinetobacter* (expressed more particularly, *Acinetobacter* organisms), or alternatively put *Acinetobacter* sp., (which includes inhibition of the growth of an *Acinetobacter* population, as well as growth of a single *Acinetobacter* organism), said method comprising using said antibiotic together with (in conjunction or combination with) an alginate oligomer.

More particularly, the using step may comprise contacting the *Acinetobacter* organisms with an alginate oligomer at the same or substantially the same time or prior to contacting the

*Acinetobacter* organisms with an antibiotic, e.g. a macrolide antibiotic, in an amount effective to improve the efficacy of an antibiotic, e.g. a macrolide antibiotic, and in particular the effectiveness (or efficacy) of an antibiotic, e.g. a macrolide antibiotic, to inhibit the growth of the *Acinetobacter* organisms. In particular, the step of contacting the *Acinetobacter* organism with the alginate oligomer may include administering the alginate oligomer to a subject, and in particular to a subject in need of such treatment (e.g. a subject infected with, suspected to be infected with, or at risk of infection with *Acinetobacter* (or expressed more particularly, with an *Acinetobacter* organism).

Thus, the invention provides an alginate oligomer for use together with (or in combination or conjunction with) at least one antibiotic in treating a subject infected, suspected to be infected, or at risk of infection, with *Acinetobacter* (or expressed more particularly, with an *Acinetobacter* organism).

This aspect of the invention also provides a method of treating a subject infected, suspected to be infected, or at risk of infection, with *Acinetobacter*, said method comprising administering an effective amount of an antibiotic to said subject together with an effective amount of an alginate oligomer.

By "use together" it is particularly meant that a pharmaceutically effective amount of the alginate oligomer and a pharmaceutically effective amount of the antibiotic are administered in a manner that results in the *Acinetobacter* (more particularly the *Acinetobacter* organisms, or population thereof) being contacted with an alginate oligomer at the same, or substantially the same, time or prior to being contacted with the antibiotic. Any clinically acceptable dosing regime may be used to achieve this. The skilled man would be able to take into account any relevant variable factors (e.g. the routes of administration, the bioavailability, and the pharmacokinetics of the oligomer and the antibiotic being used, the subject's physical state, the location of the bacterium, etc.) in order to design an appropriate dosing regime for a particular subject. In one embodiment, a pharmaceutically effective amount of the alginate oligomer is administered at the same or substantially the same time as or prior to administering a pharmaceutically effective amount of the antibiotic. In other embodiments the oligomer is administered separately to and after the antibiotic. The skilled man would readily be able to design his dosing regime to maximise the improvement in the effectiveness of the antibiotic against *Acinetobacter* organisms. He would also be able to select optimal combinations of the two active agents depending on the particular clinical situation he is faced with.

"Use together" does not imply that the respective agents are present in the same formulation or composition, and accordingly even if used, or administered, at the same or substantially the same time, the alginate oligomer and antibiotic need not, indeed most likely will not, be present in the same composition or formulation, but may be administered separately. Thus "separate" use/administration includes use/administration at the same or substantially the same time, or at different times, e.g. sequentially, or at different time intervals according to the desired dosage or usage regime.

The term "infected with" (or "infected by") is used broadly herein to indicate that the subject may comprise, or contain, or carry, the *Acinetobacter* organism in question, i.e. that the *Acinetobacter* may simply be present in or on the subject, and this may include any site or location in or on the body of the subject. It is not necessary that the infection of the subject be manifest as a clinical disease (i.e. that the infection result in clinical symptoms in the subject), although this is of course encompassed. A subject who is suspected to be infected with or who is at risk of infection by an *Acinetobacter* may be a subject who has been exposed to the organism or to a subject infected with an *Acinetobacter*, or a subject presenting with clinical signs or symptoms of *Acinetobacter* infection (in the case of a suspected infection), or a subject who is susceptible to infection by *Acinetobacter*, whether generally (e.g. due to the clinical status of the subject) or particularly due to the *Acinetobacter* in question.

Alternatively put, the invention provides the use of an alginate oligomer for the manufacture of a medicament for use together with at least one antibiotic in treating a subject infected, suspected to be infected, or at risk of infection, with *Acinetobacter* (or with an *Acinetobacter* organism or an *Acinetobacter* sp.).

The medicament may further comprise the antibiotic (or antibiotics). The medicament may be in the form of a single composition or formulation comprising the alginate oligomer and antibiotic(s) or separate compositions or formulations may be prepared and used, each containing the alginate oligomer or the antibiotic(s), respectively.

Thus in a more particular aspect the present invention provides the use of an alginate oligomer and at least one antibiotic for the manufacture of a medicament for use in treating a subject infected, suspected to be infected, or at risk of infection, with *Acinetobacter* (or with an *Acinetobacter* organism or an *Acinetobacter* sp).

As noted above, the antibiotic may be applied or administered separately from the alginate oligomer.

Thus a further aspect the present invention provides a product containing an alginate oligomer and an antibiotic (e.g. one or more antibiotics) as a combined preparation for separate, simultaneous or sequential use in treating a subject infected, suspected to be infected, or at risk of infection, with *Acinetobacter* (or with an *Acinetobacter* organism or an *Acinetobacter* sp).

The antibiotic may be applied or administered simultaneously with the alginate oligomer or sequentially. As noted above, in one embodiment the antibiotic is administered at the same or substantially the same time as the alginate oligomer, and in another embodiment it is administered after the alginate oligomer. In other embodiments the oligomer is administered separately to and after the antibiotic. Included within the scope of "substantially the same time" is application or administration of the antibiotic immediately or almost immediately before or after the alginate oligomer. The term "almost immediately" may be read as including application or administration within one hour of the previous application or administration, preferably within 30 minutes. However the antibiotic may be applied or administered at least 1 hour, at least 3 hours, or at least 6 hours or more after the alginate oligomer. In these embodiments the antibiotic can be applied or administered with or without a further application of an alginate oligomer. The alginate oligomer can be applied or administered in a plurality of applications prior to or with the antibiotic, including as noted above, an application or administration immediately or almost immediately after the antibiotic. In other embodiments the antibiotic(s) may conveniently be applied or administered before the alginate oligomer, e.g. at least 1 hour, at least 3 hours, at least 6 hours before the alginate oligomer. In these embodiments the alginate oligomer can be applied or administered with or without a further application of the antibiotic. The antibiotic can be applied or administered in a plurality of applications prior to or with the alginate oligomer including as noted above, an application or administration immediately or almost immediately after the oligomer.

Conveniently the macrolide antibiotic is applied or administered simultaneously with the oligomer or almost immediately before or after the oligomer. However the macrolide antibiotic may be applied or administered at least 1 hour, at least 3 hours, at least 6 hours after the oligomer. In these embodiments the macrolide antibiotic can be applied or administered with or without a further application of an alginate oligomer. The oligomer can be applied or administered in a plurality of applications prior to or with the macrolide antibiotic.

The antibiotic may be any antibiotic. Classes of antibiotics and representative constituents thereof include, but are not limited to the aminoglycosides (e.g. amikacin, gentamicin, kanamycin, neomycin, netilmicin, streptomycin, tobramycin); the carbacephems (e.g. loracarbef); the 1st generation cephalosporins (e.g. cefadroxil, cefazolin, cephalexin); 2nd generation cephalosporins (e.g. cefaclor, cefamandole, cephalexin, cefoxitin, cefprozil, cefuroxime); 3rd generation cephalosporins (e.g. cefixime, cefdinir, cefditoren, cefoperazone, cefotaxime, cefpodoxime, ceftazidime, ceftibuten, ceftizoxime, ceftriaxone); 4th generation cephalosporins (e.g. cefepime); the macrolides (e.g. azithromycin, clarithromycin, dirithromycin, erythromycin, troleandomycin); the monobactams (e.g. aztreonam); the penicillins (e.g. amoxicillin, ampicillin, carbenicillin, cloxacillin, dicloxacillin, nafcillin, oxacillin, penicillin G, penicillin V, piperacillin, ticarcillin); the polypeptide antibiotics (e.g. bacitracin, colistin, polymyxin B); the quinolones (e.g. ciprofloxacin, enoxacin, gatifloxacin, levofloxacin, lomefloxacin, moxifloxacin, norfloxacin, ofloxacin, trovafloxacin); the sulfonamides (e.g. mafenide, sulfacetamide, sulfamethizole, sulfasplazine, sulfisoxazole, trimethoprim-sulfamethoxazole); the tetracyclines (e.g. demeclocycline, doxycycline, minocycline, oxytetracycline, tetracycline); the glycylcyclines (e.g. tigecycline); the carbapenems (e.g. imipenem, meropenem, ertapenem, doripenem, panipenem/betamipron, biapenem, PZ-601); other antibiotics include chloramphenicol; clindamycin, ethambutol; fosfomycin; isoniazid; linezolid; metronidazole; nitrofurantoin; pyrazinamide; quinupristin/dalfopristin; rifampin; spectinomycin; and vancomycin.

In preferred embodiments of the methods of the invention the antibiotic used is an antibiotic selected from, the macrolides, the β-lactams, which may include the carbapenems and/or monobactams and/or carbacephems, the tetracyclines, and the quinolones. In other embodiments the antibiotic classes may include the aminoglycosides and/or the polypeptide antibiotics. More specifically, in these embodiments the antibiotic may be selected from the macrolides, the monobactams, the carbapenems, the carbacephems, the 3rd and 4th generation cephalosporins, the tetracyclines and the quinolones, and optionally the aminoglycosides and/or the polypeptide antibiotics. In more particular representative embodiments the antibiotic may be selected from macrolides, β-lactams, tetracyclines and quinolones e.g. macrolides, monobactams, carbapenems, carbacephems, 3rd and 4th generation cephalosporins, tetracyclines and quinolones. In more particular representative embodiments the antibiotic may be selected from macrolides, β-lactams and quinolones e.g. macrolides, monobactams, carbapenems, carbacephems, 3rd and 4th generation cephalosporins and quinolones. For example, the antibiotic may be selected from amikacin, gentamicin, kanamycin, neomycin, netilmicin, streptomycin, tobramycin, azithromycin, clarithromycin, dirithromycin, erythromycin, roxithromycin, telithromycin, CarbomycinA, josamycin, kitasamycin, midecamicine, oleandomycin, spiramycin, tylosin, troleandomycin, aztreonam, imipenem, meropenem, ertapenem, doripenem, panipenem/betamipron, biapenem, PZ-601, cefixime, cefdinir, cefditoren, cefoperazone, cefotaxime, cefpodoxime, ceftazidime, ceftibuten, ceftizoxime, ceftriaxone, cefepime, demeclocycline, doxycycline, minocycline, oxytetracycline, tetracycline, bacitracin, colistin, polymyxin B, ciprofloxacin, enoxacin, gatifloxacin, levofloxacin, lomefloxacin, moxifloxacin, norfloxacin, ofloxacin, and trovafloxacin. In particular, the antibiotic may selected from ceftazidime, imipenem/cilastatin, meropenem, aztreonam, oxytetracycline, azithromycin, clarithromycin, dirithromycin, erythromycin, roxithromycin, spiramycin and ciprofloxacin, and it is particularly preferred that the antibiotic is selected from ceftazidime, imipenem/cilastatin, meropenem, aztreonam, azithromycin, clarithromycin, dirithromycin, erythromycin, roxithromycin, spiramycin and ciprofloxacin. More preferably the antibiotic is selected from aztreonam, azithromycin, clarithromycin, dirithromycin, erythromycin, roxithromycin, spiramycin and ciprofloxacin. In other embodiments the antibiotic used is not tobramycin, amikacin and/or colistin. In other embodiments the antibiotic used is not an aminoglycoside or a polypeptide antibiotic. In other embodiments the antibiotic used is not an antibiotic that has a positive charge under the conditions in which it will be used with the alginate oligomer, e.g. antibiotics with at least 3, e.g. at least 4, 5, 6 or 7 amino (—NH2) groups. Particularly preferred are macrolides, β-lactams, tetracyclines and quinolones e.g. macrolides, monobactams, carbapenems, 3rd and 4th generation cephalosporins, tetracyclines and quinolones; e.g. ceftazidime, imipenem/cilastatin, meropenem, aztreonam, oxytetracycline, azithromycin, clarithromycin, dirithromycin, erythromycin, roxithromycin, spiramycin and ciprofloxacin.

In other preferred embodiments the antibiotic is a macrolide antibiotic and may be selected from azithromycin, clarithromycin, dirithromycin, erythromycin, roxithromycin, telithromycin, CarbomycinA, josamycin, kitasamycin, midecamicine, oleandomycin, spiramycin, troleandromycin, tylosin. Preferably the macrolide antibiotic is an azalide macrolide, preferably azithromycin, or is selected from clarithromycin, dirithromycin, erythromycin, roxithromycin or spiramycin.

As noted above, alginates typically occur as polymers of an average molecular weight of at least 35,000 Daltons i.e. approximately 175 to 190 monomer residues, although typically much higher and an alginate oligomer according to the present invention may be defined as a material obtained by fractionation (i.e. size reduction) of an alginate polymer, commonly a naturally occurring alginate. An alginate oligomer can be considered to be an alginate of an average molecular weight of less than 35,000 Daltons (i.e. less than approximately 190 or less than 175 monomer residues), in particular an alginate of an average molecular weight of less than 30,000 Daltons (i.e. less than approximately 175 or less than 150 monomer residues) more particularly an average molecular weight of less than 25,000 or 20,000 Daltons (i.e. less than approximately 135 or 125 monomer residues or less than approximately 110 or 100 monomer residues).

Viewed alternatively, an oligomer generally comprises 2 or more units or residues and an alginate oligomer for use according to the invention will typically contain 2 to 100 monomer residues, preferably 2 to 75, preferably 2 to 50, more preferably 2 to 40, 2 to 35 or 2 to 30 residues. Thus, an alginate oligomer for use according to the invention will typically have an average molecular weight of 350 to 20,000 Daltons, preferably 350 to 15,000 Daltons, preferably 350 to 10,000 Daltons and more preferably 350 to 8000 Daltons, 350 to 7000 Daltons, or 350 to 6,000 Daltons.

Alternatively put, the alginate oligomer may have a degree of polymerisation (DP), or a number average degree of polymerisation (DPn) of 2 to 100, preferably 2 to 75, preferably 2 to 50, more preferably 2 to 40, 2 to 35, 2 to 30, 2 to 28, 2 to 25, 2 to 22, 2 to 20, 2 to 18, 2 to 17, 2 to 15 or 2 to 12.

Other representative ranges (whether for the number of residues, DP or DPn) include any one of 3, 4, 5, 6, 7, 8, 9, 10 or 11 to any one of 50, 45, 40, 39, 38, 37, 36, 35, 34, 33, 32, 31, 30, 29, 28, 27, 26, 25, 24, 23, 22, 21, 20, 19, 18, 17, 16, 15, 14, 13 or 12.

Other representative ranges (whether for the number of residues, DP or DPn) include any one of 8, 9, 10, 11, 12, 13, 14 or 15 to any one of 50, 45, 40, 39, 38, 37, 36, 35, 34, 33, 32, 31, 30, 29, 28, 27, 26, 25, 24, 23, 22, 21, 20, 19, 18, 17 or 16.

Other representative ranges (whether for the number of residues, DP or DPn) include any one of 11, 12, 13, 14, 15, 16, 17 or 18 to any one of 50, 45, 40, 39, 38, 37, 36, 35, 34, 33, 32, 31, 30, 29, 28, 27, 26, 25, 24, 23, 22, 21, 20 or 19.

An alginate oligomer will, as noted above, contain (or comprise) guluronate or guluronic acid (G) and/or mannuronate or mannuronic acid (M) residues or units. An alginate oligomer according to the invention will preferably be composed solely, or substantially solely (i.e. consist essentially of) uronate/uronic acid residues, more particularly solely or substantially solely of G and/or M residues. Alternatively expressed, in the alginate oligomer of use in the present invention, at least 80%, more particularly at least 85, 90, 95 or 99% of the monomer residues may be uronate/uronic acid residues, or, more particularly G and/or M residues. In other words, preferably the alginate oligomer will not comprise other residues or units (e.g. other saccharide residues, or more particularly other uronic acid/uronate residues).

The alginate oligomer is preferably a linear oligomer.

More particularly, in a preferred embodiment at least 30% of the monomer residues of the alginate oligomer are G residues (i.e. guluronate or guluronic acid). In other words the alginate oligomer will contain at least 30% guluronate (or guluronic acid) residues. Specific embodiments thus include alginate oligomers with (e.g., containing) 30 to 70% G (guluronate) residues or 70 to 100% G (guluronate) residues. Thus, a representative alginate oligomer for use according to the present invention may contain at least 70% G residues (i.e. at least 70% of the monomer residues of the alginate oligomer will be G residues).

Preferably at least 50% or 60%, more particularly at least 70% or 75%, even more particularly at least 80, 85, 90, 91, 92, 93, 94, 95, 96, 97, 98 or 99% of the monomer residues are guluronate. In one embodiment the alginate oligomer may be an oligoguluronate (i.e. a homooligomer of G, or 100% G)

In a further preferred embodiment, the above described alginates of the invention have a primary structure wherein the majority of the G residues are in so called G-blocks. Preferably at least 50%, more preferably at least 70 or 75%, and most preferably at least 80, 85, 90, 92 or 95% of the G residues are in G-blocks. A G block is a contiguous sequence of at least two G residues, preferably at least 3 contiguous G residues, more preferably at least 4 or 5 contiguous G residues, most preferably at least 7 contiguous G residues.

In particular at least 90% of the G residues are linked 1-4 to another G residue. More particularly at least 95%, more preferably at least 98%, and most preferably at least 99% of the G residues of the alginate are linked 1-4 to another G residue.

The alginate oligomer of use in the invention is preferably a 3- to 35-mer, more preferably a 3- to 28-mer, in particular a 4- to 25-mer, especially a 6- to 22-mer, in particular an 8- to 20-mer, especially a 10- to 15-mer, e.g. having a molecular weight in the range 350 to 6400 Daltons or 350 to 6000 Daltons, preferably 550 to 5500 Daltons, preferably 750 to 5000 Daltons, and especially 750 to 4500 Daltons or 2000 to 3000 Daltons. Other representative alginate oligomers include, as mentioned above, oligomers with 7, 8, 9, 10, 11 or 12 to 50, 45, 40, 35, 28, 25, 22 or 20 residues.

It may be a single compound or it may be a mixture of compounds, e.g. of a range of degrees of polymerization. As noted above, the monomeric residues in the alginate oligomer, may be the same or different and not all need carry electrically charged groups although it is preferred that the majority (e.g. at least 60%, preferably at least 80% more preferably at least 90%) do. It is preferred that a substantial majority, e.g. at least 80%, more preferably at least 90% of the charged groups have the same polarity. In the alginate oligomer, the ratio of hydroxyl groups to charged groups is preferably at least 2:1, more especially at least 3:1.

The alginate oligomer of the invention may have a degree of polymerisation (DP), or a number average degree of polymerisation ($DP_n$), of 3-28, 4-25, 6-22, 8-20 or 10-15, or 5 to 18 or 7 to 15 or 8 to 12, especially 10.

The alginate oligomer of the invention may have a degree of polymerisation (DP), or a number average degree of polymerisation (DPn), of 8-50, 8-40, 8-35, 8-30, 8-28, 8-25, 8-22, 8-20, 8-18, 8-16 or 8-14.

The alginate oligomer of the invention may have a degree of polymerisation (DP), or a number average degree of polymerisation (DPn), of 9-50, 9-40, 9-35, 9-30, 9-28, 9-25, 9-22, 9-20, 9-18, 9-16 or 9-14.

The alginate oligomer of the invention may have a degree of polymerisation (DP), or a number average degree of polymerisation (DPn), of 10-50, 10-40, 10-35, 10-30, 10-28, 10-25, 10-22, 10-20, 10-18, 10-16 or 10-14.

The alginate oligomer of the invention may have a degree of polymerisation (DP), or a number average degree of polymerisation (DPn), of 12-50, 12-40, 12-35, 12-30, 12-28, 12-25, 12-22, 12-20, 12-18, 12-16 or 12-14.

The alginate oligomer of the invention may have a degree of polymerisation (DP), or a number average degree of polymerisation (DPn), of 15-50, 15-40, 15-35, 15-30, 15-28, 15-25, 15-22, 15-20, 15-18 or 15-16.

The alginate oligomer of the invention may have a degree of polymerisation (DP), or a number average degree of polymerisation (DPn), of 18-50, 18-40, 18-35, 18-30, 18-28, 18-25, 18-22 or 18-20.

Preferably the alginate oligomer of the invention is substantially free, preferably essentially free, of alginate oligomers having a degree of polymerisation outside of the ranges disclosed herein. This may be expressed in terms of the molecular weight distribution of the alginate oligomer of the invention, e.g. the percentage of each mole of the alginate oligomer being used in accordance with the invention which has a DP outside the relevant range.

The molecular weight distribution is preferably such that no more than 10% preferably no more than 9, 8, 7, 6, 5, 4, 3, 2 or 1% mole has a DP of three, two or one higher than the relevant upper limit for $DP_n$. Likewise it is preferred that no more than 10% preferably no more than 9, 8, 7, 6, 5, 4, 3, 2 or 1% mole has a DP below a number three, two or one smaller than the relevant lower limit for $DP_n$.

Suitable alginate oligomers are described in WO2007/039754, WO2007/039760, WO 2008/125828, and PCT/GB2008/003607, the disclosures of which are explicitly incorporated by reference herein in their entirety.

Representative suitable alginate oligomers have a $DP_n$ in the range 5 to 30, a guluronate/galacturonate fraction ($F_G$) of at least 0.80, a mannuronate fraction ($F_M$) of no more than 0.20, and at least 95 mole % of DP no more than 25.

Further suitable alginate oligomers have a number average degree of polymerization in the range 7 to 15 (preferably 8 to 12), a guluronate/galacturonate fraction ($F_G$) of at least 0.85 (preferably at least 0.90), a mannuronate fraction ($F_M$) of no more than 0.15 (preferably no more than 0.10), and having at least 95% mole with a degree of polymerization less than 17 (preferably less than 14).

Further suitable alginate oligomers have a number average degree of polymerization in the range 5 to 18 (especially 7 to 15), a guluronate/galacturonate fraction ($F_G$) of at least 0.80 (preferably at least 0.85, especially at least 0.92), a mannuronate fraction ($F_M$) of no more than 0.20 (preferably no more than 0.15, especially no more than 0.08), and having at least 95% mole with a degree of polymerization less than 20 (preferably less than 17).

Further suitable alginate oligomers have a number average degree of polymerization in the range 5 to 18, a guluronate/galacturonate fraction ($F_G$) of at least 0.92, a mannuronate fraction ($F_M$) of no more than 0.08, and having at least 95% mole with a degree of polymerization less than 20.

Further suitable alginate oligomers have a number average degree of polymerization in the range 5 to 18 (preferably 7 to 15, more preferably 8 to 12, especially about 10), a guluronate/galacturonate fraction ($F_G$) of at least 0.80 (preferably at least 0.85, more preferably at least 0.90, especially at least 0.92, most especially at least 0.95), a mannuronate fraction ($F_M$) of no more than 0.20 (preferably no more than 0.15, more preferably no more than 0.10, especially no more than 0.08, most especially no more than 0.05), and having at least 95% mole with a degree of polymerization less than 20 (preferably less than 17, more preferably less than 14).

Further suitable alginate oligomers have a number average degree of polymerization in the range 7 to 15 (preferably 8 to 12), a guluronate/galacturonate fraction ($F_G$) of at least 0.92 (preferably at least 0.95), a mannuronate fraction ($F_M$) of no more than 0.08 (preferably no more than 0.05), and having at least 95% mole with a degree of polymerization less than 17 (preferably less than 14).

Further suitable alginate oligomers have a number average degree of polymerization in the range 5 to 18, a guluronate/galacturonate fraction ($F_G$) of at least 0.80, a mannuronate fraction ($F_M$) of no more than 0.20, and having at least 95% mole with a degree of polymerization less than 20.

Further suitable alginate oligomers have a number average degree of polymerization in the range 7 to 15, a guluronate/galacturonate fraction ($F_G$) of at least 0.85, a mannuronate fraction ($F_M$) of no more than 0.15, and having at least 95% mole with a degree of polymerization less than 17.

Further suitable alginate oligomers have a number average degree of polymerization in the range 7 to 15, a guluronate/galacturonate fraction ($F_G$) of at least 0.92, a mannuronate fraction ($F_M$) of no more than 0.08, and having at least 95% mole with a degree of polymerization less than 17.

It will thus be seen that a particular class of alginate oligomers favoured according to the present invention is alginate oligomers defined as so-called "high G" or "G-block" oligomers i.e. having a high content of G residues or G-blocks (e.g. wherein at least 70% of the monomer residues are G, preferably arranged in G-blocks). However, other types of alginate oligomer may also be used, including in particular "high M" or "M-block" oligomers or MG-block oligomers, as described further below. Accordingly, it is alginate oligomers with high proportions of a single monomer type, and with said monomers of this type being present predominantly in contiguous sequences of that monomer type, that represent oligomers that are particularly preferred, e.g. oligomers wherein at least 70% of the monomer residues in the oligomer are G residues linked 1-4 to another G-residue, or more preferably at least 75%, and most preferably at least 80, 85, 90, 92, 93, 94, 95, 96, 97, 98, 99% of the monomers residues of the oligomer are G residues linked 1-4 to another G residue. This 1-4 linkage of two G residues can be alternatively expressed as a guluronic unit bound to an adjacent guluronic unit.

In a further embodiment more than 50% of the monomer residues of the alginate oligomer may be M residues (i.e. mannuronate or mannuronic acid). In other words the alginate oligomer will contain more than 50% mannuronate (or mannuronic acid) residues. Specific embodiments thus include alginate oligomers with (e.g. containing) 50 to 70% M (mannuronate) residues or e.g. 70 to 100% M (mannuronate) residues. Further specific embodiments also include oligomers containing 71 to 85% M residues or 85 to 100% M residues. Thus, a representative alginate oligomer for use according to this embodiment of the present invention will contain more than 70% M residues (i.e. more than 70% of the monomer residues of the alginate oligomer will be M residues).

In other embodiments at least 50% or 60%, more particularly at least 70% or 75%, even more particularly at least 80, 85, 90, 95 or 99% of the monomer residues are mannuronate. In one embodiment the alginate oligomer may be an oligomannuronate (i.e. a homooligomer of M, or 100% M).

In a further embodiment, the above described alginates of the invention have a primary structure wherein the majority of the M residues are in so called M-blocks. In this embodiment preferably at least 50%, more preferably at least 70 or 75%, and most preferably at least 80, 85, 90 or 95% of the M residues are in M-blocks. An M block is a contiguous sequence of at least two M residues, preferably at least 3 contiguous M residues, more preferably at least 4 or 5 contiguous M residues, most preferably at least 7 contiguous M residues.

In particular, at least 90% of the M residues are linked 1-4 to another M residue. More particularly at least 95%, more preferably at least 98%, and most preferably at least 99% of the M residues of the alginate are linked 1-4 to another M residue.

Other preferred oligomers are alginate oligomers wherein at least 70% of the monomer residues in the oligomer are M residues linked 1-4 to another M-residue, or more preferably at least 75%, and most preferably at least 80, 85, 90, 92, 93, 94, 95, 96, 97, 98, 99% of the monomers residues of the oligomer are M residues linked 1-4 to another M residue. This 1-4 linkage of two M residues can be alternatively expressed as a mannuronic unit bound to an adjacent mannuronic unit.

In a still further embodiment, the alginate oligomers of the invention comprise a sequence of alternating M and G residues. A sequence of at least three, preferably at least four, alternating M and G residues represents an MG block. Preferably the alginate oligomers of the invention comprise an MG block. Expressed more specifically, an MG block is a sequence of at least three contiguous residues consisting of G and M residues and wherein each non-terminal (internal) G residue in the contiguous sequence is linked 1-4 and 4-1 to an M residue and each non-terminal (internal) M residue in the contiguous sequence is linked 1-4 and 4-1 to a G residue. Preferably the MG block is at least 5 or 6 contiguous residues, more preferably at least 7 or 8 contiguous residues.

In a further embodiment the minority uronate in the alginate oligomer (i.e. mannuronate or guluronate) is found predominantly in MG blocks. In this embodiment preferably at least 50%, more preferably at least 70 or 75% and most preferably at least 80, 85, 90 or 95% of the minority uronate monomers in the MG block alginate oligomer are present in MG blocks. In another embodiment the alginate oligomer is arranged such that at least 50%, at least 60%, at least 70%, at least 80%, at least 85%, at least 90%, at least 95%, at least 99%, e.g. 100% of the G and M residues in the oligomer are arranged in MG blocks.

Although at its broadest, the invention extends to embodiments wherein at least 1% but less than 100% of the monomer residues of the oligomer are G residues (i.e. guluronate or guluronic acid), more particularly, and as defined further below, at least 30% of the monomer residues are G residues. Thus, at its broadest the MG block containing alginate oligomer may contain at least 1%, but less than 100%, guluronate (or guluronic acid) residues, but generally the MG block containing alginate oligomer will contain at least 30% (or at least 35, 40 or 45% or 50% G) but less than 100% G. Specific embodiments thus include MG block containing alginate oligomers with (e.g. containing) 1 to 30% G (guluronate) residues, 30 to 70% G (guluronate) residues or 70 to 99% G (guluronate) residues. Thus, a representative MG block containing alginate oligomer for use according to the present invention may contain more than 30%, but less than 70%, G residues (i.e. more than 30%, but less than 70%, of the monomer residues of the MG block alginate oligomer will be G residues).

Preferably more than 30%, more particularly more than 35% or 40%, even more particularly more than 45, 50, 55, 60 or 65%, but in each case less than 70%, of the monomer residues of the MG block containing alginate oligomer are guluronate. Alternatively, less than 70%, more preferably less than 65% or 60%, even more preferably less than 55, 50, 45, 40 or 35%, but in each case more than 30% of the monomer residues of the MG block containing alginate oligomer are guluronate. Any range formed by any combination of these values may be chosen. Therefore for instance the MG block containing alginate oligomer can have e.g. between 35% and 65%, 40% and 60% or 45% and 55% G residues.

In another embodiment the MG block containing alginate oligomer may have approximately equal amounts of G and M residues (e.g. ratios between 65% G/35% M and 35% G/65% M, for instance 60% G/40% M and 40% G/60% M; 55% G/45% M and 45% G/55% M; 53% G/47% M and 47% G/53% M; 51% G/49% M and 49% G/51% M; e.g. about 50% G and about 50% M) and these residues are arranged predominantly, preferably entirely or as completely as possible, in an alternating MG pattern (e.g. at least 50% or at least 60, 70, 80, 85, 90 or 95% or 100% of the M and G residues are in an alternating MG sequence).

In certain embodiments the terminal uronic acid residues of the oligomers of the invention do not have a double bond, especially a double bond situated between the $C_4$ and $C_5$ atom. Such oligomers may be described as having saturated terminal uronic acid residues. The skilled man would be able to prepare oligomers with saturated terminal uronic acid residues without undue burden. This may be through the use of production techniques which yield such oligomers, or by converting (saturating) oligomers produced by processes that yield oligomers with unsaturated terminal uronic acid residues.

The alginate oligomer will typically carry a charge and so counter ions for the alginate oligomer may be any physiologically tolerable ion, especially those commonly used for charged drug substances, e.g. sodium, potassium, ammonium, chloride, mesylate, meglumine, etc. Ions which promote alginate gelation e.g. group 2 metal ions may also be used.

While the alginate oligomer may be a synthetic material generated from the polymerisation of appropriate numbers of guluronate and mannuronate residues, the alginate oligomers of use in the invention may conveniently be obtained, produced or derived from natural sources such as those mentioned above, namely natural alginate source materials.

Polysaccharide to oligosaccharide cleavage to produce the alginate oligomer useable according to the present invention may be performed using conventional polysaccharide lysis techniques such as enzymatic digestion and acid hydrolysis. In one favoured embodiment acid hydrolysis is used to prepare the alginate oligomers of the invention. In other embodiments enzymic digestion is used with an additional processing step(s) to saturate the terminal uronic acids in the oligomers. Oligomers may then be separated from the polysaccharide breakdown products chromatographically using an ion exchange resin or by fractionated precipitation or solubilisation or filtration. U.S. Pat. No. 6,121,441 and WO 2008/125828, which are explicitly incorporated by reference herein in their entirety, describe a process suitable for preparing the alginate oligomers of use in the invention. Further information and discussion can be found in for example in "Handbooks of Hydrocolloids", Ed. Phillips and Williams, CRC, Boca Raton, Fla., USA, 2000, which textbook is explicitly incorporated by reference herein in its entirety.

The alginate oligomers may also be chemically modified, including but not limited to modification to add charged groups (such as carboxylated or carboxymethylated glycans) and alginate oligomers modified to alter flexibility (e.g. by periodate oxidation).

Alginate oligomers (for example oligoguluronic acids) suitable for use according to the invention may conveniently be produced by acid hydrolysis of alginic acid from, but not limited to, *Laminaria hyperbora* and *Lessonia nigrescens*, dissolution at neutral pH, addition of mineral acid reduce the pH to 3.4 to precipitate the alginate oligomer (oligoguluronic acid), washing with weak acid, resuspension at neutral pH and freeze drying.

The alginates for production of alginate oligomers of the invention can also be obtained directly from suitable bacterial sources e.g. *Pseudomonas aeruginosa* or *Azotobacter vinelandii*.

In embodiments where alginate oligomers which have primary structures in which the majority of the G residues are arranged in G-blocks rather than as single residues are required, algal sources are expected to be most suitable on account of the fact that the alginates produced in these organisms tend to have these structures. The bacterial sources may more suitable for obtaining alginate oligomers of different structures.

The molecular apparatus involved in alginate biosynthesis in *Pseudomonas fluorescens* and *Azotobacter vinelandii* has been cloned and characterised (WO 94/09124; Ertesvåg, H., et al, Metabolic Engineering, 1999, Vol 1, 262-269; WO 2004/011628; Gimmestad, M., et al (supra); Remminghorst and Rehm, Biotechnology Letters, 2006, Vol 28, 1701-1712; Gimmestad, M. et al Journal of Bacteriology, 2006, Vol 188 (15), 5551-5560) and alginates of tailored primary structures can be readily obtained by manipulating these systems.

The G content of alginates (for example an algal source material) can be increased by epimerisation, for example with mannuronan C-5 epimerases from *A. vinelandii* or other epimerase enzymes. Thus, for example in vitro epimerisation may be carried out with isolated epimerases from *Pseudomonas* or *Azotobacter*, e.g. AlgG from *Pseudomonas fluorescens* or *Azotobacter vinelandii* or the AlgE enzymes (AlgE1 to AlgE7) from *Azotobacter vinelandii*. The use of epimerases from other organisms that have the capability of producing alginate, particularly algae, is also specifically contemplated. The in vitro epimerisation of low G alginates with *Azoto-*

*bacter vinelandii* AlgE epimerases is described in detail in Ertesvåg et al (supra) and Strugala et al (Gums and Stabilisers for the Food Industry, 2004, 12, The Royal Society of Chemistry, 84-94).

To obtain G-block containing alginates or alginate oligomers, epimerisation with one or more *Azotobacter vinelandii* AlgE epimerases other than $AlgE_4$ is preferred as these enzymes are capable of producing G block structures. On the other hand AlgE4 epimerase can be used to create alginates or alginate oligomers with alternating stretches of M/G sequence or primary structures containing single G residue as it has been found that this enzyme seems preferentially to epimerise individual M residues so as to produce single G residues linked to M residues rather than producing G blocks. Particular primary structures can be obtained by using different combinations of these enzymes.

Mutated versions of these enzymes or homologues from other organisms are also specifically contemplated as of use. WO 94/09124 describes recombinant or modified mannuronan C-5 epimerase enzymes (AlgE enzymes) for example encoded by epimerase sequences in which the DNA sequences encoding the different domains or modules of the epimerases have been shuffled or deleted and recombined. Alternatively, mutants of naturally occurring epimerase enzymes, (AlgG or AlgE) may be used, obtained for example by site directed or random mutagenesis of the AlgG or AlgE genes.

A different approach is to create *Pseudomonas* and *Azotobacter* organisms that are mutated in some or all of their epimerase genes in such a way that those mutants produce alginates of the required structure for subsequent alginate oligomer production, or even alginate oligomers of the required structure and size (or molecular weight). The generation of a number of *Pseudomonas fluorescens* organisms with mutated AlgG genes is described in detail in WO 2004/011628 and Gimmestad, M., et al, 2003 (supra). The generation of a number of *Azotobacter vinelandii* organisms with mutated AlgE genes is disclosed in Gimmestad, M., et al, 2006 (supra). The skilled man would be able to use this teaching to produce new mutants that could be used to give rise to the alginate oligomers of the invention without undue burden.

A further approach is to delete or inactivate the endogenous epimerase genes from an *Azotobacter* or a *Pseudomonas* organism and then to introduce one or more exogenous epimerase genes, which may or may not be mutated (i.e. may be wild-type or modified) and the expression of which may be controlled, for example by the use of inducible or other "controllable promoters". By selecting appropriate combinations of genes, alginates of predetermined primary structure can be produced.

A still further approach would be to introduce some or all of the alginate biosynthesis machinery of *Pseudomonas* and/or *Azotobacter* into a non-alginate producing organism (e.g. *E. coli*) and to induce the production of alginate from these genetically modified organisms.

When these culture-based systems are used, the primary structure of the alginate or alginate oligomer products can be influenced by the culture conditions. It is well within the capabilities of the skilled man to adjust culture parameters such as temperature, osmolarity, nutrient levels/sources and atmospheric parameters in order to manipulate the primary structure of the alginates produced by a particular organism.

References to "G residues/G" and "M residues/M" or to guluronic acid or mannuronic acid, or guluronate or mannuronate are to be read interchangeably as references to guluronic acid/guluronate and mannuronic acid/mannuronate (specifically α-L-guluronic acid/guluronate and β-D-mannuronic acid/mannuronate), and further include derivatives thereof in which one or more available side chains or groups have been modified without resulting in activity (e.g. antibiotic effect enhancing or synergistic activity) that is substantially lower than that of the unmodified oligomer. Common saccharide modifying groups would include acetyl, sulphate, amino, deoxy, alcohol, aldehyde, ketone, ester and anhydro groups. The alginate oligomers may also be chemically modified to add charged groups (such as carboxylated or carboxymethylated glycans), and to alter flexibility (e.g. by periodate oxidation). The skilled man would be aware of still further chemical modifications that can be made to the monosaccharide subunits of oligosaccharides and these can be applied to the alginate oligomers of the invention.

The *Acinetobacter* organism can be from any *Acinetobacter* species, e.g. *Acinetobacter baumannii, Acinetobacter baylyi, Acinetobacter bouvetii, Acinetobacter calcoaceticus, Acinetobacter gerneri, Acinetobacter grimontii, Acinetobacter haemolyticus, Acinetobacter johnsonii, Acinetobacter junii, Acinetobacter lwoffii, Acinetobacter parvus, Acinetobacter radioresistens, Acinetobacter schindleri, Acinetobacter tandoii, Acinetobacter tjernbergiae, Acinetobacter towneri, Acinetobacter ursingii*. Preferably it is *Acinetobacter baumannii, Acinetobacter haemolyticus, Acinetobacter johnsonii, Acinetobacter junii, Acinetobacter radioresistens, Acinetobacter lwoffii, Acinetobacter tandoii, Acinetobacter tjernbergiae, Acinetobacter towneri*, or *Acinetobacter ursingii*, more preferably *Acinetobacter baumannii* and *Acinetobacter lwoffii*, most preferably *Acinetobacter baumannii*.

The *Acinetobacter* may be determined to be resistant to one or more antibiotics with activity against Gram-negative bacteria, e.g. an antibiotic selected from the macrolides, the β-lactams (which may include the carbapenems, carbacephems and monobactams), the tetracyclines, the polypeptide antibiotics and the quinolones. In other embodiments the classes may include the aminoglycosides. In still further embodiments the classes may include the macrolides, the β-lactams and the quinolones. It will be noted that the invention may result in the overcoming of resistance to one or more classes to which the *Acinetobacter* is resistant, but it is not necessarily implied that resistance is overcome to all of the classes of antibiotic to which an *Acinetobacter* may be resistant. Thus for example resistance to a macrolide and/or a β-lactam and/or a quinolone may be overcome in an MDR strain which is also resistant to other antibiotics e.g. aminoglycosides.

More specifically, in these embodiments the antibiotic may be selected from the macrolides, the monobactams, the carbapenems, carbacephems, the 3rd and 4th generation cephalosporins, the tetracyclines, the polypeptide antibiotics and the quinolones. In more particular representative embodiments the bacteria may be resistant to an antibiotic selected from macrolides, β-lactams, and quinolones e.g. an antibiotic selected from macrolides, monobactams, carbapenems, carbacephems, 3rd and 4th generation cephalosporins, and quinolones. In other embodiments the antibiotic classes listed above may also include the aminoglycosides. For example, the antibiotic may be selected from amikacin, gentamicin, kanamycin, neomycin, netilmicin, streptomycin, tobramycin, azithromycin, clarithromycin, dirithromycin, erythromycin, roxithromycin, telithromycin, CarbomycinA, josamycin, kitasamycin, midecamicine, oleandomycin, spiramycin, tylosin, troleandomycin, aztreonam, imipenem, meropenem, ertapenem, doripenem, panipenem/betamipron, biapenem, PZ-601, cefixime, cefdinir, cefditoren, cefoperazone, cefotaxime, cefpodoxime, ceftazidime, ceftibuten, ceftizoxime, ceftriaxone, cefepime, demeclocycline, doxycycline, minocycline, oxytetracycline, tetracycline, bacitracin, colistin, polymyxin B, ciprofloxacin, enoxacin, gatifloxacin, levofloxacin, lomefloxacin, moxifloxacin, norfloxacin, ofloxacin, and/or trovafloxacin. In particular, the *Acinetobacter* organism may be resistant to one or more antibiotics selected from amikacin, tobramycin, ceftazidime, imipenem/cilastatin, meropenem, aztreonam, oxytetracycline, colistin, azithromycin, clarithromycin, dirithromycin, erythromycin, roxithromycin, spiramycin and ciprofloxacin, and it is particularly preferred that the *Acinetobacter* organism is resistant to one or more antibiotics selected from ceftazidime, imipenem/cilastatin, meropenem, aztreonam, azithromycin, clarithromycin, dirithromycin, erythromycin, roxithromycin, spiramycin and ciprofloxacin. More preferably the *Acinetobacter* organism is resistant to one or more antibiotics selected from aztreonam, azithromycin, clarithromycin, dirithromycin, erythromycin, roxithromycin, spiramycin and ciprofloxacin.

By "resistant to an antibiotic" it is meant that the bacterium displays a substantially greater tolerance (reduced susceptibility) to an antibiotic as compared to a reference bacterium sensitive to the antibiotic or a typical, or a wild type, version of the bacterium. Whilst resistance may be acquired or developed (e.g. by transfer from another bacterium or by mutation—the term "acquired" as used herein includes any means or mechanism by which resistance arises), it may also be intrinsic (or innate) to the organism. Such a substantially greater tolerance may be a statistically significant decrease in susceptibility to the antibiotic, as measured for example in standard assays, such as MIC assays. In some cases, a bacterium can be completely unaffected by exposure to an antibiotic. In this instance the bacterium can be considered fully resistant to that antibiotic.

A representative reference bacterium is Oxford *Staphylococcus aureus* (NCTC 6571) although many others are known in the art and are readily available. Typical, or wild type, versions of a bacterium can be obtained easily from laboratories and culture collections throughout the world.

Susceptibility (and conversely resistance and tolerance) to antibiotic can be measured in any convenient way, e.g. with dilution susceptibility tests and/or disk diffusion tests. The skilled man would appreciate that the extent of the difference in tolerance/susceptibility sufficient to constitute resistance will vary depending on the antibiotic and organism under test and the test used However, a resistant bacterium will preferably be at least twice, e.g. at least 3, 4, 5, 6, 10, 20, or 50 times as tolerant to the antibiotic as the reference bacterium sensitive to the antibiotic or a typical or a wild type version of the bacterium. Preferably resistance of a particular bacteria to an antibiotic is determined using bacteria which are not in a biofilm or which do not have a biofilm phenotype.

The *Acinetobacter* may be determined to be multidrug resistant (MDR), e.g. the *Acinetobacter* displays resistance to more than two (e.g. more than 3, more than 5 or more than 10) antibiotics with activity against Gram-negative bacteria. Preferably the *Acinetobacter* organism is resistant to at least 3, or at least 4, 5, 6, 7, 8, 9 or 10 antibiotic classes, e.g. those described above. As noted above, antibiotics in different classes are structurally and/or functionally different. In other embodiments the *Acinetobacter* organism targeted by the method of the invention can be any *Acinetobacter* organism that has extreme drug resistance, which according to the present invention means that the bacterium is resistant to the majority of, or all, antibiotics. In particular, extreme drug resistant bacterium are resistant to at least one antibiotic of last resort (e.g. vancomycin, linezolid, etc.). The skilled man would be aware of examples of antibiotics of last resort.

In preferred embodiments the antibiotic used in the method of the invention is an antibiotic to which the *Acinetobacter* organism being targeted displays resistance. In accordance with the invention the alginate oligomers of the invention improve the effectiveness of the antibiotic used against the target *Acinetobacter* organism. If that organism is resistant to the antibiotic, the invention can viewed as a method for overcoming resistance to said antibiotic in said *Acinetobacter* organism. In preferred embodiments of the methods of the invention the antibiotic used is an antibiotic selected from the macrolides, the β-lactams, the tetracyclines, and the quinolones. In a further embodiment the polypeptide antibiotics and/or the aminoglycosides may be included. In alternative embodiments the antibiotic does not include an aminoglycoside and/or a polypeptide antibiotic (e.g colistin).

"Overcoming resistance" should be construed accordingly as a measurable reduction in the above-described indicators of the resistance (or measurable increase in susceptibility or measurable decrease in tolerance) to the antibiotic displayed by the *Acinetobacter*. Therefore "overcoming resistance" can alternatively be expressed as "reducing resistance". It is a reference to the observed phenotype of the target *Acinetobacter* and should not necessarily be considered to equate to a reversal, to any extent, at the mechanistic level of any particular resistance mechanism. As can be seen from the Examples, alginate oligomers and antibiotics have a combinatorial, e.g. synergistic, effect that makes *Acinetobacter* with a phenotype that is resistant to an antibiotic more susceptible to that antibiotic. In one embodiment the alginate oligomer will measurably reduce the MIC value of the resistant *Acinetobacter* to the antibiotic, e.g. the MIC value will be at least 50%, 25%, 20%, 15%, 10%, 5%, 2% or 1% of the MIC value of the *Acinetobacter* for the antibiotic before treatment in accordance with the invention.

Thus use of alginate oligomers according to the present invention may render usable (or effective) an antibiotic previously thought not to be usable/effective against a particular *Acinetobacter*, or an antibiotic which is not normally effective against a given *Acinetobacter*. It may also enable an antibiotic to be used at a reduced dose.

However, as noted above, it is not required, or implied, that all of the resistance of any given resistant, e.g. MDR, strain is overcome. The invention may for example be effective in overcoming resistance to certain classes of antibiotic in an given strain (e.g to macrolides and/or quinolones and/or β-lactams) and this may be clinically useful, even though resistance to other antibiotics may remain.

The effects of alginate oligomers in overcoming resistance to antibiotics or in potentiating (etc.) the effects of antibiotics may be seen irrespective of the mechanism of resistance to the antibiotic in question. Nevertheless, good results have been observed with ciprofloxacin. Resistance to this antibiotic may involve accumulation of mutations, in particular in the genes encoding DNA gyrase or topoisomerase IV. Without wishing to be bound by theory, the alginate oligomers of the invention may therefore affect this accumulation process, e.g. by preventing, slowing or halting it. However, it is not to assumed from or implied by this, that alginate oligomers may have any effect on any mechanism of resistance.

The *Acinetobacter* may also be a strain that has been found previously, or is also found, in a patient (e.g. a human patient) or in a healthcare institution (e.g. a hospital). As noted above, *Acinetobacter* are prevalent in Middle Eastern countries and accordingly the *Acinetobacter* may be any such strain or species. For example, the *Acinetobacter* may be a strain found in Libya. Alternatively viewed, the *Acinetobacter* organism targeted by the invention is a clinically relevant *Acinetobacter* organism, e.g. an *Acinetobacter* organism that is known to be associated with disease and/or infection in subjects; especially diseases and infections that are unresponsive to an antibiotic or antibiotic class, preferably at least 3 structurally and/or functionally different antibiotics, or at least 3 antibiotic classes, more particularly at least 4, 5, 6, 7 8, 9 or 10 structurally and/or functionally different antibiotics or classes, conventionally used in the treatment of that disease and/or infection. More particularly, the *Acinetobacter* organism targeted by the invention may be from a clinically relevant MDR strain of *Acinetobacter*. The *Acinetobacter* organism may cause or result in clinically significant or clinically important infections, in other words infections which are the cause of significant clinical problems. For instance, the *Acinetobacter* organism could be a *Acinetobacter* organism associated with nosocomial infections, infections in the respiratory tract of patients, e.g. patients suffering from cystic fibrosis, chronic obstructive pulmonary disease, congestive obstructive airway disease/congestive obstructive airway pneumonia (COAD/COAP), pneumonia, emphysema, bronchitis and sinusitis; infections in chronic wounds (including burns), device related infections associated with implantable or prosthetic medical devices e.g. prosthetic valve endocarditis or infection of lines or catheters or artificial joints or tissue replacements or endotracheal or tracheotomy tubes. Notably, as noted above, *Acinetobacter* infections acquired in military situations, for example in battlegrounds e.g. in the Middle East, are increasingly becoming a problem, and may be susceptible to treatment according to the present invention.

The *Acinetobacter* organism targeted by the method of the invention may be the same as a bacterium that has previously been isolated from a subject. Thus, the *Acinetobacter* organism is preferably a clinical strain or a clinical isolate. The *Acinetobacter* organism targeted by the method of the invention may be present in or on a subject. The *Acinetobacter* organism may be known or found to be resistant to an antibiotic e.g. to be MDR, or the *Acinetobacter* organism may have developed resistance or MDR during the subject's treatment. The *Acinetobacter* organism to be treated according to the present invention will generally not be a conventional laboratory or reference strain.

Preferably, the *Acinetobacter* species is *Acinetobacter baumannii*, the alginate oligomers are oligomers with a primary structure wherein the majority of the G residues are in G-blocks and the antibiotic is a macrolide, e.g. the antibiotic is azithromycin.

In other preferred embodiments the *Acinetobacter* species is *Acinetobacter baumannii* or *Acinetobacter lwoffii*, and the antibiotic is selected from the macrolides, the β-lactams, the tetracyclines, and the quinolones, e.g. azithromycin, clarithromycin, dirithromycin, erythromycin, roxithromycin, spiramycin, aztreonam, imipenem, meropenem, ceftazidime, oxytetracycline or ciprofloxacin, especially azithromycin, clarithromycin, dirithromycin, erythromycin, roxithromycin, spiramycin, aztreonam, meropenem, or ceftazidime.

The method of the invention may entail contacting the *Acinetobacter* with more than one antibiotic. The additional antibiotic(s) can be any antibiotic, e.g. those listed above. The additional antibiotic(s) may be an antibiotic to which the *Acinetobacter* is susceptible. The additional antibiotic(s) may be an antibiotic to which the *Acinetobacter* is resistant. The additional antibiotic(s) may be used together with (in conjunction or combination with) the first or other antibiotics and/or the alginate oligomer. More particularly, the step of using may comprise contacting the *Acinetobacter* with an alginate oligomer at the same or substantially the same time or prior to contacting the *Acinetobacter* with some or all of the antibiotics in an amount effective to inhibit the growth and/or viability of the *Acinetobacter*.

As noted above the antibiotic(s) may conveniently be applied or administered simultaneously with the alginate oligomer, or immediately or almost immediately before or after the alginate oligomer. However, the antibiotic(s) may be applied or administered at a different time point, e.g. at least 1 hour, at least 3 hours, at least 6 hours after the alginate oligomer. It is within the skill of the medical practitioner to develop dosage regimes which optimise the effect of the alginate oligomer and antibiotic. In these embodiments the antibiotic(s) can be applied or administered with or without a further application of an alginate oligomer. The alginate oligomer can be applied or administered in a plurality of applications prior to or with the antibiotic(s). In other embodiments the antibiotic(s) may conveniently be applied or administered before the alginate oligomer, e.g. at least 1 hour, at least 3 hours, at least 6 hours before the alginate oligomer. In these embodiments the alginate oligomer can be applied or administered with or without a further application of the antibiotic(s). The antibiotic(s) can be applied or administered in a plurality of applications prior to or with the alginate oligomer. The skilled man can easily determine what would be an appropriate dosing regime for the alginate oligomer and antibiotic(s) he intends to use.

Preferred antibiotic combinations can be two or more from colistin, ciprofloxacin, meropenem, ceftazidime, aztreonam, azithromycin, clarithromycin, dirithromycin, erythromycin, roxithromycin, spiramycin and imipenem/cilastatin, amikacin, gentamicin, oxytetracycline, tobramycin and vancomycin. More particularly, these may be selected from ciprofloxacin, meropenem, ceftazidime, aztreonam, azithromycin, clarithromycin, dirithromycin, erythromycin, roxithromycin, spiramycin imipenem/cilastatin or oxytetracycline, and still more particularly from ciprofloxacin, meropenem, ceftazidime, aztreonam, azithromycin, clarithromycin, dirithromycin, erythromycin, roxithromycin and spiramycin.

The *Acinetobacter* population may comprise any of the above mentioned *Acinetobacter* species and may be homogenous or heterogeneous. An *Acinetobacter* population is considered to be of at least 1000 organisms, e.g. at least $10^5$, $10^6$, $10^7$, $10^8$ or $10^9$ organisms. The *Acinetobacter* organism or the *Acinetobacter* population may also share its location with another microorganism.

The term "microorganism" as used herein includes any microbial organism, that is any organism that is microscopic, namely too small to be seen by the naked eye. In particular as used herein the term includes viruses, as well as the organisms more typically thought of as microorganisms, particularly bacteria, fungi, archaea, algae and protists. The term thus particularly includes organisms that are typically unicellular, but which may have the capability of organising into simple cooperative colonies or structures such as filaments, hyphae or mycelia (but not true tissues) under certain conditions. The microorganism may be prokaryotic or eukaryotic, and may be from any class, genus or species of microorganism. Examples of prokaryotic microorganisms include, but are not limited to, bacteria, including the mycoplasmas, (e.g. Gram-positive, Gram-negative bacteria or Gram test non-responsive bacteria) and archaeobacteria. Eukaryotic microorganisms include fungi, algae and others that are, or have been, classified in the taxonomic kingdom Protista or regarded as protists, and include, but are not limited to, for example, protozoa, diatoms, protoophyta, and fungus-like molds. The microorganism may be aerobic or anaerobic. The microorganism may be pathogenic or, non-pathogenic, or a be spoilage or an indicator microorganism. In particular preferred embodiments the microorganism is pathogenic.

Examples of genera or species of bacteria include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobspirillum, Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chiamydophila, Chromobacterium, Chyseobacterium, Chryseomonas, Citrobacter, Clostridium, Collinsella, Comamonas, Corynebacterium, Coxiella, Cryptobacterium, DeMa, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Globicatella, Gemella, Gordona, Haemophilus, Hafnia, Helicobacter, Helococcus, Holdemania, Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Staphylococcus, Stenotrophomonas, Stomatococcus, Streptobacillus, Streptococcus, Streptomyces, Succinivibrio, Sutterella, Suttonella, Tatumefla, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella*; e.g. gram-positive bacteria such as, *M. tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides, Actinomyces israelii, Propionibacterium acnes, Clostridium tetani, Clostridium perfringens, Clostridium botulinum,* and *Enterococcus* species and Gram-negative bacteria such as *Pseudomonas aeruginosa, Vibrio cholerae, Actinobacillus pleuropneumoniae, Pasteurella haemolytica, Pasteurella multocida, Legionella pneumophila, Salmonella typhi, Brucella abortus, Coxiella bumetti, Escherichia coli, Neiserria meningitidis, Neiserria gonorrhea, Haemophilus influenzae, Haemophilus ducreyi, Yersinia pestis, Yersinia enterolitica, Escherichia coli, E. hirae, Burkholderia cepacia, Burkholderia pseudomallei, Francisella tularensis, Bacteroides fragilis, Fusobascterium nucleatum, Cowdria ruminantium* and Gram non-responsive bacteria such as *Chlamydia trachomatis* and *Chlamydia psittaci.*

The microorganism may also be a, or from a, fungus, including for example fungi that may be, or may have been, classified as protista, e.g. fungi from the genera *Candida, Aspergillus, Pneumocystis, Penicillium* and *Fusarium.* Representative fungal species include, but are not limited to, *Candida albicans, Candida dubliniensis, Cryptococcus neoformans, Histoplama capsulatum, Aspergillus fumigatus, Coccidiodes immitis, Paracoccidiodes brasiliensis, Blastomyces dermitidis, Pneomocystis carnii, Penicillium marneffi, Alternaria alternate.*

The microorganism may also be an, or from an, alga, including for example algae that may be, or may have been, classified as protista. Representative algal species include *Chaetophora, Chlorella protothecoides, Coleochaete scutata, Coleochaete soluta, Cyanidioschyzon merolae Aphanochaete, Gloeotaenium, Oedogonium, Oocystis, Oscillatoria, Paradoxia multisitia, Phormidium, Chroococcus, Aphanothece, Fragillaria, Cocconis, Navicula, Cymbella, Phaeodactylum* as well as cyanobacteria (blue-green algae) and diatoms such as *Nitzschia palea.*

The microorganism may also be a protozoa, e.g. a member of the groups Amoebae, Sporozoa, Ciliates, and Flagellates. Representative protozoa include *Toxoplasma* species e.g. *Toxoplasma gondii, Plasmodium* species such as *Plasmodium falciparum, Plasmodium vivax, Plasmodium malariae. Trypanosoma* species e.g. *Trypanosoma brucei, Trypanosoma cruzi, Leishmania* species such as *Leishmania major,* and *Entamoeba* species such as *Entamoeba histolytica.*

The term "virus" covers all viruses. Thus, the virus may be an RNA virus (single or double stranded) or a DNA virus (single or double stranded). It may be an enveloped or a non-enveloped virus. The virus may target prokaryotes or eukaryotes; it may be a bacteriophage or a virus that targets plants, animals or fungi. Preferably the virus targets eukaryotes, preferably animals or plants. Representative families of viruses that target animals are the parvoviridae, papoviridae, adenoviridae, picoviridae, reoviridae, reteroviridae, coronaviridae, rhabdoviridae, paramyxoviridae, orthomyxoviridae, herpesviridae, hepadnaviridae and poxyiridae. Representative families of viruses that target plants are the bromovirus, nepovirus, comovirus, caulimovirus, reoviridae, rhabdoviridae, tobamovirus, cucumovirus, luteovirus, potexvirus and potyvirus. The virus may be any member of these families, e.g. HIV, herpes simplex virus, Epstein-Barr virus, orthopoxvirus, avipoxvirus, papillomavirus, adenovirus, parvovirus, influenza, hepatitis virus A, B, C, D and E, rabies virus, measles virus, foot-and-mouth disease virus, SARS coronavirus, rhinovirus, rotavirus, rubella virus and mumps virus.

The location of the *Acinetobacter* organism or population thereof is not restricted. The *Acinetobacter* organism or population thereof may be present on a surface. The surface is not limited and includes any surface on which an *Acinetobacter* organism or population thereof may occur. The surface may be biotic or abiotic, and inanimate (or abiotic) surfaces include any such surface which may be exposed to microbial contact or contamination. Thus particularly included are surfaces on machinery, notably industrial machinery, or medical equipment or any surface exposed to an aquatic environment (e.g. marine equipment, or ships or boats or their parts or components), or any surface exposed to any part of the environment, e.g. pipes or on buildings. Such inanimate surfaces exposed to microbial contact or contamination include in particular any part of: food or drink processing, preparation, storage or dispensing machinery or equipment, air conditioning apparatus, industrial machinery, e.g. in chemical or biotechnological processing plants, storage tanks, medical or surgical equipment and cell and tissue culture equipment. Any apparatus or equipment for carrying or transporting or delivering materials is susceptible to microbial contamination. Such surfaces will include particularly pipes (which term is used broadly herein to include any conduit or line). Representative inanimate or abiotic surfaces include, but are not limited to food processing, storage, dispensing or preparation equipment or surfaces, tanks, conveyors, floors, drains, coolers, freezers, equipment surfaces, walls, valves, belts, pipes, air conditioning conduits, cooling apparatus, food or drink dispensing lines, heat exchangers, boat hulls or any part of a boat's structure that is exposed to water, dental waterlines, oil drilling conduits, contact lenses and storage cases.

As noted above, medical or surgical equipment or devices represent a particular class of surface on which *Acinetobacter* contamination may form. This may include any kind of line, including catheters (e.g. central venous and urinary catheters), prosthetic devices e.g., heart valves, artificial joints, false teeth, dental crowns, dental caps and soft tissue implants (e.g. breast, buttock and lip implants). Any kind of implantable (or "in-dwelling") medical device is included (e.g. stents, intrauterine devices, pacemakers, intubation tubes (e.g. endotracheal or tracheostomy tubes), prostheses or prosthetic devices, lines or catheters). An "in-dwelling" medical device may include a device in which any part of it is contained within the body, i.e. the device may be wholly or partly in-dwelling.

The surface can be made of any material. For example it may be metal, e.g. aluminium, steel, stainless steel, chrome, titanium, iron, alloys thereof, and the like. The surface can also be plastic, for example, polyolefin (e.g., polyethylene, (Ultra-High Molecular Weight) polyethylene, polypropylene, polystyrene, poly(meth)acrylate, acrylonitrile, butadiene, ABS, acrylonitrile butadiene, etc.), polyester (e.g., polyethylene terephthalate, etc.), and polyamide (e.g., nylon), combinations thereof, and the like. Other examples include acetal copolymer, polyphenylsulfone, polysulfone, polythermide, polycarbonate, polyetheretherketone, polyvinylidene fluoride, poly(methyl methacrylate) and poly(tetrafluoroethylene). The surface can also be brick, tile, ceramic, porcelain, wood, vinyl, linoleum, or carpet, combinations thereof, and the like. The surfaces can also be food, for example, beef, poultry, pork, vegetables, fruits, fish, shellfish, combinations thereof, and the like. The "treatment" of any such surface (i.e. the application to any such surface of an alginate oligomer together with an antibiotic) to combat infection by an *Acinetobacter*, is encompassed by the present invention.

In an infection by an *Acinetobacter*, which may be treated according to the present invention, the *Acinetobacter* may occur on a surface in a subject. Furthermore, outside the context of medical treatment, *Acinetobacter* organisms may also occur on biotic surfaces. Thus the invention includes the treatment of biotic surfaces. A biotic or animate surface may include any surface or interface in or on an animal, plant or fungal body. It may accordingly be viewed as a "physiological" or "biological" surface. It may be any internal or external body surface, including of any tissue or organ, which, in the case of an animal body, may include haematological or haematopoietic tissue (e.g. blood). Dead or dying (e.g. necrotic) or damaged (e.g. inflamed or disrupted or broken) tissue is particularly susceptible to microbiological contamination, and such tissue is encompassed by the term "animate" or "biotic". The surface may be a mucosal or non-mucosal surface.

Representative biotic surfaces include, but are not limited to, any surface in the oral cavity (e.g. teeth, gingiva, gingival crevice, periodontal pocket) the reproductive tract (e.g. cervix, uterus, fallopian tubes), the peritoneum, middle ear, prostate, urinary tract, vascular intima, eye, i.e. any ocular tissue (e.g. the conjunctiva, corneal tissue, lachrymal duct, lachrymal gland, eyelid) the respiratory tract, lung tissue (e.g. bronchial and alveolial), heart valves, gastrointestinal tract, skin, scalp, nails and the interior of wounds, particularly chronic wounds and surgical wounds, which may be topical or internal wounds. Other surfaces include the exterior of organs, particularly those undergoing transplantation, for example, heart, lungs, kidney, liver, heart valve, pancreas, intestine, corneal tissue, arterial and venous grafts and skin.

In one aspect the surface will not be mucosal, or more particularly will not have a hyperviscous mucus coating. The skilled person will be able to determine when the mucus at a given surface is hyperviscous. In one embodiment the surface will not be the surface of a mucus-secreting tissue. More particularly in such an embodiment the surface will not be the surface of a mucus-coated tissue. The skilled person will know from his common general knowledge the tissues that secrete mucus and those that are mucus-coated.

The location may also be a location that is not a surface. In other words the *Acinetobacter* organism or population thereof can be found within an material as well as on its surface. The material can be chemically heterogeneous as well as chemically homogenous. The material can also be constructed or formed from or comprise different parts or components. The material can be a part of a larger material or entity. The material may be or comprise the materials from which the above mentioned surfaces are formed. In some instances the material can be considered to be an object, which terms covers volumes of liquids wherever found. The material may comprise any of the above described surfaces. The material may be abiotic or biotic (inanimate or animate) as is discussed above in relation to surfaces. For instance, the material might be, completely or in part, a solid, a liquid, a semi solid, a gel or a gel-sol. Thus, for example, the *Acinetobacter* organism or population thereof might be present in body fluids (e.g. blood, plasma, serum, cerebrospinal fluid, GI tract contents, semen); tissues (e.g. adrenal, hepatic, renal, pancreatic, pituitary, thyroid, immune, ovarian, testicular, prostate, endometrial, ocular, mammary, adipose, epithelial, endothelial, neural, muscle, pulmonary, epidermis, osseous); cell and tissue culture media; cell and tissue cultures; clinical/scientific waste materials (which can comprise any of the preceding materials); pharmaceuticals (e.g. tablets, pills, powders, lozenges, sachets, cachets, elixirs, suspensions, emulsions, solutions, syrups, aerosols, sprays, compositions for use in nebulisers, ointments, soft and hard gelatine capsules, suppositories, sterile injectable solutions, sterile packaged powders); animal or human food stuffs (e.g. meat, fish, shellfish, vegetables, cereals, diary products, fruit juices, vegetable juices, sauces, stocks, soups, confectionary, alcoholic beverages, condiments); personal hygiene products (e.g. toothpaste, mouthwash, shampoo, soap, deodorant, shower gel); cosmetics (e.g. lip gloss, eye shadow, foundation); drinking water supplies; waste water supplies; agricultural feedstuffs and water supplies; insecticide, pesticide and herbicide formulations; industrial lubricants and so on. Liquids, semi solids, gels or gel-sols are of note. The body fluids and tissues may be treated in vitro/ex vivo as well as it being possible to treat the same in vivo.

In certain embodiments the *Acinetobacter* organism will not be in a biofilm. In other embodiments the *Acinetobacter* organism will be in a biofilm. Put differently, the *Acinetobacter* organism will not be, or will be, in a biofilm mode of growth; or will be, or will not be, in a non-biofilm mode of growth. Data has been obtained which shows that alginate oligomers may disrupt *Acinetobacter* biofilms in vitro. For example, in the case of in vitro biofilms of *A. Baumannii*, the alginate oligomer Oligo CF-5/20 (90-95% G residues) caused approximately 80% disruption at 6 and 10%, characterised by cell death and gross morphological distortion. Alginate oligomers, particularly those defined as above as "high G" or as having a high G-block content, may be particularly effective against *Acinetobacter*, including a direct effect on the *Acinetobacter*, or an effect in disrupting an *Acinetobacter* biofilm, and may accordingly be useful against *Acinetobacter* in their own right.

Thus, in other aspects the present invention also provides an alginate oligomer (which may be any alginate oligomer as defined herein) for use in combating *Acinetobacter* infection or contamination (i.e. colonisation), or in inhibiting the growth and/or viability of *Acinetobacter*, including *Acinetobacter* biofilm, or a biofilm containing *Acinetobacter*.

By "biofilm" it is meant a community of microorganisms characterized by a predominance of sessile cells that are attached to a substratum or interface or to each other (some motile cells may also be present) and that are embedded in a matrix of extracellular polymers (more specifically extracellular polymers that they have produced) characterised in that the microorganisms of this colony exhibit an altered phenotype with respect to growth rate and gene transcription (for example as compared to their "non-biofilm" or free-floating or planktonic counterparts).

By "in a biofilm" it is meant that the *Acinetobacter* organism is within (completely or in part), on or associated with the polymer matrix of a biofilm and has an phenotype characteristic of *Acinetobacter* organisms in a biofilm (i.e. a phenotype that is altered with respect to growth rate and gene transcription, for example as compared to "non-biofilm" or free-floating or planktonic *Acinetobacter* organisms.

Viewed differently, *Acinetobacter* organisms that are "not in a biofilm" are organisms that are either in isolation, e.g. planktonic, or if in an aggregation of a plurality of organisms, that aggregation is unorganised. In each case, the individual *Acinetobacter* organisms do not exhibit an altered phenotype that is observed in their biofilm dwelling counterparts.

It is well appreciated that *Acinetobacter* organisms can form a capsule from extracellular polymers (e.g. polysaccharides) that they have produced and *Acinetobacter* organisms are typically found with such a capsule. It is also well appreciated that the simple presence of a polymer capsule of an *Acinetobacter* organism is not functionally equivalent to a biofilm mode of growth and the presence of such a capsule is therefore not in itself indicative of a biofilm phenotype. Thus, it will also be appreciated that *Acinetobacter* organisms that are "not in a biofilm" may still be in contact a matrix of extracellular polymers that they have produced (i.e. the capsule), but such organisms will not exhibit an altered phenotype that is observed in their biofilm dwelling counterparts. Thus, a given population of *Acinetobacter* organisms may have some organisms with a biofilm phenotype (e.g. will be in a biofilm mode of growth) and others may not have a biofilm phenotype (e.g. will not be in a biofilm mode of growth).

From the forgoing it is clear that the methods of the invention, i.e. those described above, have medical and non-medical applications. In particular, the invention provides a method for combating *Acinetobacter* contamination of a location (or site), in particular the treatment of an *Acinetobacter* infection in a subject, and also a method to combat a population of *Acinetobacter* organisms. Thus, the method may be an in vitro or an in vivo method. As explained in more detail below, "combating" includes both the treatment of an existing contamination or infection, and treatment to prevent a contamination or infection from occurring, i.e. both "therapeutic"/reactionary and prophylactic treatments.

Accordingly, in one aspect of the invention there is provided 4 method for the treatment of an *Acinetobacter* infection in a subject, said method comprising administering to a subject a pharmaceutically effective amount of an alginate oligomer at substantially the same time as or prior to administering a pharmaceutically effective amount of an antibiotic, e.g. a macrolide antibiotic.

Thus the invention provides an alginate oligomer for use together with (or in combination or conjunction with) an antibiotic, e.g. a macrolide antibiotic for the treatment of an *Acinetobacter* infection in a subject.

In another aspect of the invention there is provided a method for the treatment or prevention of an *Acinetobacter* infection in a subject in need of such treatment (e.g. a subject infected with, suspected to be infected with, or at risk of infection with, an *Acinetobacter* organism) said method comprising administering to a subject a pharmaceutically effective amount of an alginate oligomer together with a pharmaceutically effective amount of an antibiotic.

Thus the invention provides an alginate oligomer for use together with (or in combination or conjunction with) an antibiotic for the treatment or prevention of an *Acinetobacter* infection in a subject in need of such treatment.

As defined in more detail above, "use together" includes that a pharmaceutically effective amount of the alginate oligomer is administered at the same or substantially the same time as or prior to administering a pharmaceutically effective amount of an antibiotic, e.g. a macrolide antibiotic, but in other embodiments the oligomer is administered separately to and after the antibiotic.

Alternatively put, the invention provides the use of an alginate oligomer for the manufacture of a medicament for use together with an antibiotic, e.g. a macrolide antibiotic in the treatment of an *Acinetobacter* infection in a subject. The invention also provides the use of an alginate oligomer for the manufacture of a medicament for use together with an antibiotic in the treatment or prevention of an *Acinetobacter* infection in a subject in need thereof.

The medicament may further comprise the antibiotic, e.g. macrolide antibiotic and single or separate compositions or formulations may be provided and used, as discussed above.

This aspect of the invention also provides the use of an alginate oligomer together with an antibiotic in the manufacture of a medicament for use in the treatment of an infection of a subject by *Acinetobacter*.

Also provided according to this aspect of the invention is a product containing an alginate oligomer and an antibiotic as a combined preparation for separate, simultaneous or sequential use in the treatment or prevention of an infection of a subject by an *Acinetobacter*.

The subject may be any human or non-human animal subject, but more particularly may be a vertebrate, e.g. an animal selected from mammals, birds, amphibians, fish and reptiles. The animal may be a livestock or a domestic animal or an animal of commercial value, including laboratory animals or an animal in a zoo or game park. Representative animals therefore include dogs, cats, rabbits, mice, guinea pigs, hamsters, horses, pigs, sheep, goats, cows, chickens, turkeys, guinea fowl, ducks, geese, parrots, budgerigars, pigeons, salmon, trout, cod, haddock, sea bass and carp. Veterinary uses of the invention are thus covered. The subject may be viewed as a patient. Preferably the subject is a human.

The term "in a subject" is used broadly herein to include sites or locations inside a subject or on a subject, e.g. an external body surface, and may include in particular infection of a medical device e.g. an implanted or "in-dwelling" medical device. The term "in a patient" should be interpreted consistently with this.

The location of the *Acinetobacter* infection is not restricted and may be any of the sites or locations within an subject described above. Administering the alginate oligomer and antibiotic e.g. macrolide antibiotic to the subject preferably results in the infected location being contacted with an alginate oligomer and antibiotic e.g. macrolide antibiotic in amounts sufficient to treat the infection.

The *Acinetobacter* infection may additionally comprise any of the microorganisms described above.

The *Acinetobacter* infection may be acute, or alternatively chronic, e.g. an infection that has persisted for at least 5 or at least 10 days, particularly at least 20 days, more particularly at least 30 days, most particularly at least 40 days.

In this aspect of the invention the *Acinetobacter* infection may occur on a surface in or on the subject (i.e. a biotic surface as discussed above) and/or a surface of a medical device, particularly an implantable or "in-dwelling" medical device, representative examples of which are discussed above.

In one embodiment of this aspect the *Acinetobacter* organism is not in a biofilm (the *Acinetobacter* infection can therefore be considered to be a non-biofilm infection). In another embodiment the *Acinetobacter* organism is in a biofilm. In one embodiment the method of this aspect of the invention may comprise a step in which the subject will be diagnosed as having an *Acinetobacter* infection or being a candidate that is at risk of developing an *Acinetobacter* infection. In another embodiment, the method of this aspect of the invention may further comprise a step in which the *Acinetobacter* infection to be targeted by the treatment will be determined as not being, or involving, a biofilm (i.e. a non-biofilm infection).

In this regard the *Acinetobacter* infection may be an infection that is found at a location that is not a surface in a subject, e.g. an *Acinetobacter* infection in a body fluid, including a blood infection and a cerebrospinal fluid infection, or an infection within a tissue. This aspect of the invention therefore provides a method for the treatment of bacteraemia, septicaemia, septic shock, sepsis, meningitis, or poisoning by *Acinetobacter* derived toxins.

In particular embodiments the invention may provide for the treatment of respiratory infections, e.g. cystic fibrosis, pneumonia, COPD, COAD, COAP, bacteraemia, septicaemia, septic shock, sepsis, meningitis, or poisoning by bacterially derived toxins.

An *Acinetobacter* infection can occur in any subject but some subjects will be more susceptible to infection that others. Subjects who are susceptible to *Acinetobacter* infection include, but are not limited to, subjects whose epithelial and/or endothelial barrier is weakened or compromised, subjects whose secretion-based defenses to microbial infection have been abrogated, disrupted, weakened or undermined, and subjects who are immunocompromised, immunodeficient or immunosuppressed (i.e. a subject in whom any part of the immune system is not working normally, or is working subnormally, in other words in whom any part of the immune response, or an immune activity is reduced or impaired, whether due to disease or clinical intervention or other treatment, or in any way).

Representative examples of subjects who are susceptible to *Acinetobacter* infection include, but are not limited to, subjects with a pre-established infection (e.g. with bacteria, viruses, fungi or parasites such as protozoa), especially subjects with HIV, subjects with bacteraemia, sepsis and subjects with septic shock; subjects with immunodeficiency, e.g. subjects preparing for, undergoing or recovering from chemotherapy and/or radiotherapy, organ (e.g. bone marrow, liver, lung, heart, heart valve, kidney, etc.) transplant subjects (including autograft, allograft and xenograft patients); subjects with AIDS; subjects resident in a healthcare institution, e.g. hospital, especially subjects in intensive care or critical care (i.e. those units concerned with the provision of life support or organ support systems to patients); subjects on respiratory ventilators; subjects suffering from trauma; subjects with burns, subjects with acute and/or chronic wounds; neonatal subjects; elderly subjects; subjects with cancer (defined broadly herein to include any neoplastic condition; malignant or non-malignant), especially those with cancers of the immune system (e.g. leukaemias, lymphomas and other haematological cancers); subjects suffering from auto-immune conditions such as rheumatoid arthritis, diabetes mellitus type I, Crohn's disease, especially those undergoing immunosuppression treatment for those diseases; subjects with reduced or abrogated epithelial or endothelial secretion (e.g. mucous, tears, saliva) and/or secretion clearance (e.g. subjects with poorly functioning cilia on mucosal tissue and/or patients with hyperviscous mucous (e.g. smokers and subjects with COPD, COAP, COAD, bronchitis, cystic fibrosis, emphysema, lung cancer, asthma, pneumonia or sinusitis)) and subjects fitted with a medical device.

Thus, subjects in whom *Acinetobacter* infections may particularly be combated according to the present invention include patients who are impaired, whether due to poor perfusion, repetitive trauma, poor nutrition, poor oxygenation or white cell dysfunction.

Of particular note are subjects that have undergone physical trauma. The trauma itself might cause a weakening in or compromisation of an epithelial and/or endothelial barrier of the subject or the subject may become immunocompromised in response to the trauma (a shock response). The term "trauma" refers broadly to cellular attack by foreign bodies and/or physical injury of cells. Included among foreign bodies are microorganisms, particulate matter, chemical agents, and the like. Included among physical injuries are mechanical injuries; thermal injuries, such as those resulting from excessive heat or cold; electrical injuries, such as those caused by contact with sources of electrical potential; and radiation damage caused, for example, by prolonged, extensive exposure to infrared, ultraviolet or ionizing radiations.

Also of particular note are subjects that have a burn. Any burn, in particular a severe burn, has a significant impact on the integrity of the epithelial and/or endothelial barrier of the subject and the subject will often become immunocompromised in response to the burn (a shock response).

Typical burn-causing agents are extremes of temperature (e.g. fire and liquids and gases at extreme temperature), electricity, corrosive chemicals, friction and radiation. The extent and duration of exposure, together with the intensity/strength of the agent, result in burns of varying severity. Scalding (i.e. trauma associated with high temperature liquids and/or gases) is considered to be a burn.

Epidermal burn severity is commonly classified in two ways. Most common is the classification by degree. First-degree burns are usually limited to erythema (redness) in the general area of the injury and a white plaque at the site of injury. The cellular trauma of these burns extends only as deep as the epidermis. Second-degree burns also display erythema in the general area of the injury but with superficial blistering of the epidermis. The cellular trauma of second-degree burns involves the superficial (papillary) dermis and may also involve the deep (reticular) dermis layer. Third-degree burns are those in which the epidermis is lost with damage to the hypodermis. Damage is typically extreme including charring. Sometimes eschar, (dry, black necrotic tissue) will be present. Third-degree burns may require grafting. In fourth-degree burns catastrophic damage of the hypodermis occurs, e.g. the hypodermis is completed lost, with damage extending to the underlying muscle, tendon, and ligament tissue. Charring and eschar are observed. Grafting is required if the burn does not prove to be fatal.

Another common classification system is the classification by thickness. "Superficial thickness" burns correspond to first degree burns. The spectrum of second degree burns is covered by two classes of "partial thickness" burns. "Partial thickness-superficial" are burns that affect the epidermis only as far as the papillary dermis. "Partial thickness-deep" are burns that affect the dermis as far as the reticular dermis. "Full thickness" burns correspond to third and fourth degree burns.

Some physical injuries, e.g. some burns, and cellular attacks by foreign bodies result in the formation of a wound. More specifically a wound may be considered to be a breach in, or denudement of, a tissue. Wounds may also be caused by a spontaneously forming lesion such as a skin ulcer (e.g. a venous, diabetic or pressure ulcer), an anal fissure or a mouth ulcer.

Wounds are typically defined as either acute or chronic. Acute wounds are wounds that proceed orderly through the three recognised stages of the healing process (i.e. the inflammatory stage, the proliferative stage and the remodelling phase) without a protracted timecourse. Chronic wounds, however, are those wounds that do not complete the ordered sequence of biochemical events of the healing process because the wound has stalled in one of the healing stages. Commonly, chronic wounds are stalled in the inflammatory phase. In accordance with a particular aspect of the present invention, a chronic wound is a wound that has not healed within at least 40 days, particularly at least 50 days, more particularly at least 60 days, most particularly at least 70 days.

As discussed above, wounds are an ideal environment for *Acinetobacter* infection, particularly chronic infection, due to their lack of an epithelial barrier and the availability of substrate and surface for microbial attachment and colonisation. Problematically, infection of a wound often delays healing further and thus renders that wound more susceptible to established infection. The methods of the invention are therefore effective in the treatment and prevention of *Acinetobacter* infection of wounds and the use of the methods of the invention in the treatment of wounds, especially chronic wounds, represents one preferred aspect of the present invention.

Therefore, in an embodiment of the invention there is provided an alginate oligomer for use together with (or in combination or conjunction with) an antibiotic, e.g. a macrolide antibiotic, in the treatment or prevention of *Acinetobacter* infection, particularly chronic *Acinetobacter* infection in the above-mentioned subjects, in particular in subjects with respiratory diseases or disorders (e.g. COPD, COAD, COAP, pneumonia, emphysema, bronchitis, cystic fibrosis) wounds, burns and/or traumas, said method comprising administering a pharmaceutically effective amount of an alginate oligomer at substantially the same time as or prior to administering a pharmaceutically effective amount of an antibiotic, e.g. a macrolide antibiotic. In other embodiments the method comprises administering a pharmaceutically effective amount of an alginate oligomer after administering a pharmaceutically effective amount of an antibiotic, e.g. a macrolide antibiotic.

In an aspect of particular importance, the alginate oligomers and antibiotics, e.g. macrolide antibiotics, of the invention may be used together (or in combination or conjunction) to treat or prevent *Acinetobacter* infection in wounds, e.g. burns, for example in the treatment of *Acinetobacter* infected wounds, e.g. burns.

Through the ability to treat and prevent infection of wounds the alginate oligomers and antibiotics of the invention as defined herein can remove one of the obstacles to wound healing and therefore the alginate oligomers and antibiotics defined above are also effective in the promotion of healing of acute and chronic wounds.

By promotion of healing it is meant that the treatment accelerates the healing process of the wound in question (i.e. the progression of the wound through the three recognised stages of the healing process). The acceleration of the healing process may manifest as an increase in the rate of progression through one, two or all of the healing stages (i.e. the inflammatory stage, the proliferative stage and/or the remodelling phase). If the wound is a chronic wound that is stalled in one of the healing stages the acceleration might manifest as the restarting of the linear, sequential healing process after the stall. In other words, the treatment shifts the wound from a non-healing state to a state where the wound begins to progress through the healing stages. That progression after the restart may be at a normal rate or even a slower rate compared with the rate a normal acute wound would heal.

The alginate oligomers and antibiotics of the invention may be used together (or in combination or conjunction) to treat *Acinetobacter* infections wherever they may occur in or on the body. Thus, in another embodiment, the infection may be an *Acinetobacter* infection of a medical device, particularly an in-dwelling medical device, e.g. endotracheal and tracheotomy tubes.

The alginate oligomers and antibiotics of the invention may be used together (or in combination or conjunction) as oral healthcare agents, for example in the control of dental plaque, e.g. to reduce it or to prevent, reduce or delay its development by inhibiting growth of *Acinetobacter* organisms on teeth or dental/oral prostheses. The alginate oligomers and antibiotics of the invention may also be used together (or in combination or conjunction) in the treatment and prevention of *Acinetobacter* infections or infectious diseases involving *Acinetobacter* organisms which may occur in the oral cavity, for example gingivitis and periodontitis Conveniently, the alginate oligomers and/or antibiotics can be applied by any oral health/oral hygiene delivery system. This may be through the use of toothpastes, dental gels, dental foams and mouthwashes. Removable dentures and other removable dental prostheses may be treated outside of the oral cavity with the same compositions or other suitable pharmaceutically acceptable compositions. The alginate oligomers and/or antibiotics can also be incorporated into compositions that are applied to the oral cavity (or applied to removable dentures and other removable dental prostheses outside of the oral cavity) to form a coating that persists on surfaces over time, or that releases the alginate oligomers and/or antibiotics from the coated surfaces over time, and which inhibit the growth of *Acinetobacter* organisms in the oral cavity and on the surfaces of removable dentures and other removable dental prostheses.

Whilst the treatment of *Acinetobacter* infections of the lungs and respiratory tract and all areas of the body is generally covered by the present invention, in one embodiment, the medical uses of the invention are not directed to the treatment of (i) infections in the respiratory tract of patients suffering from COPD's (chronic obstructive pulmonary diseases), in particular the sinuses and the lungs, in particular in the treatment of cystic fibrosis, chronic obstructive pulmonary disease, emphysema, bronchitis and sinusitis; (ii) in the middle ear of patients suffering from glue ear; or (iii) in the reproductive tract of female patients with impaired fertility; or (iv) in the digestive tract of patients with digestive tract malfunction (e.g. constipation).

In specific embodiments of the invention the alginate oligomers and antibiotics, e.g. macrolide antibiotics, of the invention may be used together (or in combination or conjunction) in the treatment of *Acinetobacter*-associated native valve endocarditis, acute otitis media, chronic bacterial prostatitis, pneumonia (in particular ventilator associated pneumonia) associated with *Acinetobacter* organisms; *Acinetobacter* infections in respiratory diseases (which may include COPD, COAD, COAP, pneumonia, cystic fibrosis and asthma); and device related *Acinetobacter* infections associated with implantable or prosthetic medical devices (e.g. prosthetic valve endocarditis or infection of lines or catheters or artificial joints or tissue replacements or endotracheal or tracheotomy tubes).

In further embodiments the alginate oligomers and antibiotics of the invention are used together to control *Acinetobacter* infections in the eye, e.g. to reduce them, or prevent, reduce or delay their development. In particular, the alginate and antibiotics of the invention are used together to treat or prevent *Acinetobacter* associated bacterial conjunctivitis and the resultant keratoconjunctivitis sicca (also known as dry eye) that can result through the blockage of the lachrymal gland As mentioned previously, in one embodiment the above *Acinetobacter* infections and associated conditions are not, or do not involve, biofilm, in other words they are non-biofilm infections. In another embodiment the above *Acinetobacter* infections and associated conditions are, or do, involve biofilm In a further aspect the invention provides a method for combating *Acinetobacter* contamination of a site, said method comprising contacting the site and/or the *Acinetobacter* organism with an effective amount of an alginate oligomer at substantially the same time as or prior to administering an effective amount of an antibiotic, e.g. a macrolide antibiotic. This method can also be described as a method for combating *Acinetobacter* contamination of a site, said method comprising contacting the site and/or the *Acinetobacter* organism with an alginate oligomer together with an antibiotic.

Also provided is an alginate oligomer for use together with (or in combination or conjunction with) an antibiotic, e.g. a macrolide antibiotic for use in combating *Acinetobacter* contamination of a site. Such a method may particularly be an in vitro method, and the site may be any surface or location discussed above.

Alternatively put, this aspect the invention provides the use of an alginate oligomer for the manufacture of a medicament for use together with an antibiotic, e.g. a macrolide antibiotic, in combating *Acinetobacter* contamination of a site. The medicament may further comprise the an antibiotic, e.g. macrolide antibiotic.

"Combating contamination" includes both preventative and reactionary measures or treatments and therefore covers the prevention as well as the reduction, limitation, or elimination of contamination.

By "contamination" it is meant the unwanted presence of an *Acinetobacter* organism at a particular site or location. Contamination can be considered to cover colonisation of a location by an *Acinetobacter* organism, i.e. the establishment of an *Acinetobacter* organism at a location and the expansion of the numbers of that organism by replication or the recruitment of additional *Acinetobacter* organisms, which may be of the same or of a different type: In one embodiment the colonisation process will not involve the formation of a biofilm.

The site or location of the contamination or potential contamination is not restricted and can be any of the various sites or locations described or mentioned above, e.g. it can be in vitro or in vivo, but particularly in this aspect of the invention it will be an "in vitro" or "ex vivo" site or location (i.e. an inanimate or abiotic site or location). However, the site or location may be in a subject and in which case a pharmaceutically effective amounts of the alginate oligomer and the antibiotic, e.g. a macrolide antibiotic, are administered to the subject.

In one particular embodiment this aspect of the invention can be applied to the decontamination of clinical, scientific and industrial waste materials. In another particular embodiment this aspect of the invention can be used to decontaminant transplant tissue (e.g. heart, lungs, kidney, liver, heart valve, pancreas, intestine, corneal tissue, arterial and venous grafts and skin) and medical devices (e.g. endotracheal and tracheostomy tubes) prior to implantation. In another embodiment this aspect can be considered to cover the use of alginate oligomers together with antibiotics as anti-*Acinetobacter* preservative agents in materials, especially solutions and liquids.

In another aspect the invention provides a method to combat a population of *Acinetobacter* organisms, said method comprising contacting said organisms with an effective amount of an alginate oligomer at substantially the same time as or prior to administering an effective amount of an antibiotic, e.g. a macrolide antibiotic.

In one embodiment of this aspect the *Acinetobacter* organism or the population thereof will not be in a biofilm or will not be in the process of forming a biofilm. For Instance, the *Acinetobacter* organism or the population thereof will not be capable of biofilm formation or the plurality of organisms in the population are not of sufficient number or at a lifecycle stage that permits biofilm formation.

The population of *Acinetobacter* organisms may be homogenous (i.e. contain a single type of *Acinetobacter* organism) or may be heterogeneous (i.e. contain a plurality of types of *Acinetobacter* organism and/or other microorganisms). For example, any or all of the various microorganism described above may be found in the population. Some or all of the microorganisms in the population may be pathogenic. The population may be an established population or be a partially established population. In other words, the location to be treated has previously been colonised by at least one microorganism that has multiplied or recruited other microorganisms to establish the population.

By "combat a population of *Acinetobacter* organisms" it is meant that the formation of the population is prevented or the growth of the population is controlled.

By "control the growth of a population of *Acinetobacter* organisms" it is meant that the rate of expansion of the overall number of *Acinetobacter* organisms in the population is reduced. Preferably the rate of expansion is reduced by at least 50%, more preferably at least 75%, 85%, 95% or 99%. Most preferably the expansion is essentially stopped or reversed, i.e. the overall number of *Acinetobacter* organisms in the population is maintained or reduced. Preferably the overall number of viable *Acinetobacter* organisms in the population is reduced by at least 50%, more preferably at least 75%, 85%, 95% or 99%. Most preferably the population is substantially or completely eradicated. By substantially eradicated it is meant that the population contains few, or virtually no viable *Acinetobacter* organisms.

Control of the growth of the population can, in one embodiment, be achieved by controlling the rate of replication of the *Acinetobacter* organisms in the population. In this regard, the rate of replication of the *Acinetobacter* organisms in the population is preferably reduced by at least 50%, more preferably at least 75%, 85%, 95% or 99%. Viewed differently, preferably replication substantially ceases or virtually stops.

Alternatively, or in addition, population growth may be controlled by killing some or all of the *Acinetobacter* organisms in the population.

By "prevent the formation of an *Acinetobacter* population" it is meant that a small number (sub-population number) of *Acinetobacter* organisms are prevented from expanding to reach population size, e.g. by preventing replication or killing the *Acinetobacter* organisms already present or that are added to those already present.

The site or location of the population of *Acinetobacter* organisms is not restricted and the various locations described above apply here also.

Thus, medical uses encompassed by the present invention may include the use of alginate oligomers and antibiotics, e.g. macrolide antibiotics, to combat *Acinetobacter* populations within a subject. In this aspect the invention accordingly provides a method to combat a population of *Acinetobacter* organisms in a subject, said method comprising contacting said organisms with a pharmaceutically effective amount of an alginate oligomer at substantially the same time as or prior to administering a pharmaceutically effective amount of an antibiotic, e.g. a macrolide antibiotic.

The antibiotic may be applied or administered simultaneously with the alginate oligomer or sequentially. As noted above, in one embodiment the antibiotic is administered at the same or substantially the same time as the alginate oligomer, and in another embodiment it is administered after the alginate oligomer. In other embodiments the oligomer is administered separately to and after the antibiotic. Included within the scope of "substantially the same time" is application or administration of the antibiotic immediately or almost immediately before or after the alginate oligomer. The term "almost immediately" may be read as including application or administration within one hour of the previous application or administration, preferably within 30 minutes. However the antibiotic may be applied or administered at least 1 hour, at least 3 hours, or at least 6 hours or more after the alginate oligomer. In these embodiments the antibiotic can be applied or administered with or without a further application of an alginate oligomer. The alginate oligomer can be applied or administered in a plurality of applications prior to or with the antibiotic, including as noted above, an application or administration immediately or almost immediately after the antibiotic. In other embodiments the antibiotic(s) may conveniently be applied or administered before the alginate oligomer, e.g. at least 1 hour, at least 3 hours, at least 6 hours before the alginate oligomer. In these embodiments the alginate oligomer can be applied or administered with or without a further application of the antibiotic. The antibiotic can be applied or administered in a plurality of applications prior to or with the Also provided is an alginate oligomer for use together with (or in combination or conjunction with) an antibiotic, e.g. a macrolide antibiotic, for use in combating an *Acinetobacter* population in a subject.

Alternatively put, this aspect the invention provides the use of an alginate oligomer for the manufacture of a medicament for use together with an antibiotic, e.g. a macrolide antibiotic, in combating an *Acinetobacter* population in a subject. The medicament may further comprise the an antibiotic, e.g. a macrolide antibiotic.

In one embodiment the method of this aspect of the invention may comprise a step in which the subject will be diagnosed as a candidate that would benefit from having a population of *Acinetobacter* organisms within it combated. In another embodiment the method of the invention may further comprise a step in which the population of *Acinetobacter* organisms to be combated will be determined as not being, or in, or involving a biofilm.

As noted above, the alginate oligomer may improve the efficacy of the antibiotic against *Acinetobacter* organisms, and in particular the efficacy (or effectiveness) of the antibiotic in inhibiting the growth of *Acinetobacter* organisms.

Improving the efficacy of the antibiotic includes any aspect of improving or enhancing the effectiveness of the antibiotic against *Acinetobacter* organisms, e.g. so that the anti-Acinetobacter effect of the antibiotic is increased or enhanced in any way over the effect of the antibiotic seen in the absence of the alginate oligomer. This may be seen for example in a stronger effect of the antibiotic in inhibiting growth of *Acinetobacter* organisms, requiring less antibiotic to achieve the same effect seen in the absence of alginate oligomer, or a increased effectiveness seen as increased speed or rate of action, an inhibitory effect being seen in less time than in the absence of oligomer.

By "growth of *Acinetobacter* organisms" it is meant both an increase in the size of an *Acinetobacter* organism or in the amount and/or volume of the constituents of an *Acinetobacter* organism (e.g. the amount of nucleic acid, the amount of protein, the number of nuclei, the numbers or size of organelles, the volume of cytoplasm) and an increase in the numbers of *Acinetobacter* organisms i.e. an increase in the replication of *Acinetobacter* organisms.

Typically growth of an *Acinetobacter* organism is accompanied by the enlargement of the organism. The growth of *Acinetobacter* organisms can be measured with routine techniques. For instance, microscopic examination of microorganism morphology over time, or assays to measure changes in the quantities of protein or nucleic acid (e.g. DNA) in general, or the changes in the quantities of specific proteins or nucleic acids, can be used. The skilled man would easily be able to select suitable markers to follow. Conveniently, so called house keeping genes (e.g. β-actin, GAPDH (glyceraldehyde 3-phosphate dehydrogenase), SDHA (succinate dehydrogenase), HPRT1 (hypoxanthine phosphoribosyl transferase 1), HBS1L (HBS1-like protein), AHSP (alpha-haemoglobin stabilising protein), and β2M (beta-2-microglobulin)), 16S RNA and virus genes, and their expression products can be monitored.

By "replication of *Acinetobacter* organisms" it is meant the act by which *Acinetobacter* organisms reproduce. Typically this is by binary fission where a microorganism divides into two. To support the division of the microorganism into two, binary fission is normally preceded by enlargement of the dividing microorganism and an increase in the amount and/or volume of cellular constituents. Replication results in an increase in the number of cells and so may be followed by any method of assessing microorganism numbers in a population.

Another option is to follow the process in real time by visual examination with a microscope. The time it takes for a microorganism to replicate (i.e. produce another version of itself) is the generation time. Generation time will depend on the conditions in which the *Acinetobacter* organism is found. The rate of replication can be expressed in terms of the generation time.

By "inhibiting the growth of *Acinetobacter* organisms" it is meant that measurable growth (e.g. replication) of an *Acinetobacter* organism, or the rate thereof, is reduced. Preferably measurable growth (e.g. replication) of an *Acinetobacter* organism, or the rate thereof, is reduced by at least 50%, more preferably at least 60%, 70%, 80% or 90%, e.g. at least 95%. Preferably, measurable growth (e.g. replication) is ceased. Growth in terms of microbial size increase or expansion etc. may be inhibited independently of replication and vice versa.

The references to "improving the effectiveness of a antibiotic to inhibit the growth and/or viability of *Acinetobacter* organisms" etc. accordingly may include that the alginate oligomer renders the antibiotic, at least twice as, or at least four times, at least eight times, at least sixteen times or at least thirty two times more effective at inhibiting bacterial growth and/or viability (e.g. acting as a bacteriostatic or bactericidal agent). Put in a different way, the oligomer may at least double, at least quadruple, at least octuple, at least sexdecuple or at least duotrigenuple the effectiveness of the antibiotic to inhibit growth and/or viability of *Acinetobacter* organisms. The inhibitory effect of the antibiotic can conveniently be measured by assessing the Minimum Inhibitory Concentration (MIC), i.e. that concentration of antibiotic that completely inhibits growth of the *Acinetobacter* organisms. A halving of the MIC corresponds to a doubling in the inhibitory effect of the antibiotic. A quartering of the MIC corresponds to a quadrupling of the inhibitory effect.

This aspect also allows the concentration of the antibiotic administered to a subject or applied to a location to be reduced whilst maintaining the same effectiveness against *Acinetobacter* organisms. This can be beneficial if the antibiotic is expensive or associated with side effects. Minimising the use of antibiotics is also desirable to minimise development of resistance. In accordance with the invention the use of an alginate oligomer as described above, i.e. together with the antibiotic, e.g. at the same or substantially the same time or prior to administering the antibiotic, permits the antibiotic to be used at a concentration that is less than 50%, less than 25%, less than 10% or less than 5% of the amount normally administered/applied to achieve a particular level of inhibition of the growth and/or viability of *Acinetobacter* organisms in the absence of the alginate oligomer.

In this aspect the alginate oligomers may be any of those discussed and in particular those stated as preferred above and the alginate oligomers will be contacted with the *Acinetobacter* organisms and/or their location at a local concentration of at least 2%, at least 4%, at least 6%, at least 8% or at least 10% weight by volume.

The term "contacting" encompasses any means of delivering the alginate oligomer and the antibiotic to the *Acinetobacter* organism, whether directly or indirectly, and thus any means of applying the alginate oligomer and the antibiotic to the *Acinetobacter* organism or exposing the *Acinetobacter* organism to the alginate oligomer and the antibiotic e.g. applying the alginate oligomer and the antibiotic directly to the *Acinetobacter* organism, or administering the alginate oligomer and the antibiotic to a subject within which or on which the *Acinetobacter* organism is present, e.g. subjects with an *Acinetobacter* infection.

More particularly the *Acinetobacter* organism will be contacted with an effective amount of the alginate oligomer and the antibiotic, more particularly an amount of the alginate oligomer and an amount of the antibiotic that together (or in combination or conjunction) inhibit the growth and/or viability of *Acinetobacter* organisms and therefore treat or prevent the infection/contamination.

An "effective amount" of the alginate oligomer and the antibiotic is that amount of alginate oligomer and that amount of the antibiotic that together (or in combination or conjunction) provide measurable inhibition of the growth and/or viability of an *Acinetobacter* organism or population thereof. In certain embodiments the "effective amount" of the alginate oligomer can be considered to be that amount effective to improve the efficacy of an antibiotic, and in particular the effectiveness (or efficacy) of an antibiotic to inhibit the growth and/or viability of an *Acinetobacter* organism or population thereof.

A "pharmaceutically effective" amount of the alginate oligomer and the antibiotic is that amount of alginate oligomer and that amount of the antibiotic that together (or in combination or conjunction) provide a measurable inhibition of the growth and/or viability of an *Acinetobacter* organism or population thereof in or on a subject and/or a measurable treatment or prevention of the *Acinetobacter* infection being targeted.

The skilled man would easily be able to determine what an effective/pharmaceutically effective amount of alginate oligomer and antibiotic would be on the basis of routine dose response protocols and, conveniently, the routine techniques for assessing microbial growth inhibition etc., as discussed above. The skilled man would, without undue burden, also be able to optimise these amounts to maximise the combinatorial effects of the alginate oligomer and antibiotic in his target system.

Suitable doses of alginate oligomer and antibiotic will vary from subject to subject and can be determined by the physician or veterinary practitioner in accordance with the weight, age and sex of the subject, the severity of the condition, the mode of administration and also the particular alginate oligomer or antibiotic selected. Typically the alginate oligomers of the invention will be applied to the location undergoing treatment at a local concentration of at least 0.5%, preferably at least 2% or at least 4%, more preferably at least 6% and most preferably at least 10% weight by volume. Typically the antibiotic of the invention will be applied to the location undergoing treatment at a local concentration of at least 0.03125 µg/ml, preferably at least 0.0625, 0.125, 0.25, 0.5, 1, 2, 4, 8, 16, 32, 64, 128, 256, 512, 1024, 2048 or 4096 µg/ml.

"Treatment" when used in relation to the treatment of a medical condition/infection in a subject in accordance with the invention is used broadly herein to include any therapeutic effect, i.e. any beneficial effect on the condition or in relation to the infection. Thus, not only included is eradication or elimination of the infection, or cure of the subject or infection, but also an improvement in the infection or condition of the subject. Thus included for example, is an improvement in any symptom or sign of the infection or condition, or in any clinically accepted indicator of the infection/condition (for example a decrease in wound size or an acceleration of healing time). Treatment thus includes both curative and palliative therapy, e.g. of a pre-existing or diagnosed infection/condition, i.e. a reactionary treatment.

"Prevention" as used herein refers to any prophylactic or preventative effect. It thus includes delaying, limiting, reducing or preventing the condition (which reference includes infection and contamination, as applicable, in the different aspects of the invention) or the onset of the condition, or one or more symptoms or indications thereof, for example relative to the condition or, symptom or indication prior to the prophylactic treatment. Prophylaxis thus explicitly includes both absolute prevention of occurrence or development of the condition, or symptom or indication thereof, and any delay, in the onset or development of the condition or symptom or indication, or reduction or limitation on the development or progression of the condition or symptom or indication.

Specifically, the alginate oligomers and antibiotics of the invention can be taken together (or in combination or conjunction) as a prophylactic treatment, for example to prevent, or at least minimise the risk, of infection or contamination by *Acinetobacter*.

The aspect of the invention concerning the combating (treatment or prevention) of *Acinetobacter* infection is of particular utility in the care of hospitalised patients as the risk of contracting an *Acinetobacter* nosocomial infection (commonly known as hospital related/acquired infection or healthcare-associated infection) can be minimised with a prophylactic regime of the alginate oligomers and antibiotics defined herein. This aspect of the invention is also of particular utility in the care of subjects suffering from trauma, subjects with a burn and subjects with wounds, all of which, as discussed above, are more susceptible to *Acinetobacter* infection than a subject that is not affected similarly.

Generally, subjects in need of treatment or prophylaxis according to the invention will be diagnosed as suffering or at risk from *Acinetobacter* infection, e.g. identified as having or at risk of developing an *Acinetobacter* infection.

Specifically, the alginate oligomers and antibiotics of the invention can be taken together (or in combination or conjunction) as a prophylactic treatment to prevent, or at least minimise the risk, of developing an *Acinetobacter* infection, including for example the *Acinetobacter* infection of wounds; *Acinetobacter*-associated native valve endocarditis, acute otitis media, chronic bacterial prostatitis, periodontitis; *Acinetobacter* infections of the respiratory tract and lungs (e.g. cystic fibrosis, COPD, COAD, COAP, pneumonia, or other respiratory diseases) or infection of a medical (e.g. in-dwelling) medical device.

The invention encompasses the use of a single alginate oligomer or a mixture (multiplicity/plurality) of different alginate oligomers. Thus, for example, a combination of different alginate oligomers (e.g. two or more) may be used.

The invention encompasses the use of a single antibiotic or a mixture (multiplicity/plurality) of different antibiotics. Thus, for example, a combination of different antibiotics (e.g. two or more) may be used.

In one advantageous embodiment of the invention the alginate oligomers and antibiotic may be used in the methods of the invention in conjunction or combination with a further anti-microbial agent (hereinafter "further anti-microbial agent")

In the context of a medical use, such an anti-microbial agent may be any clinically-useful anti-microbial agent and particularly an antibiotic or an antiviral or antifungal agent. In the context of non-clinical uses, the anti-microbial agent may again be any anti-microbial agent used for such purposes, e.g. any disinfectant or antiseptic or cleaning or sterilising agent. The agents may be used separately, or together in the same composition, simultaneously or sequentially or separately, e.g. at any desired time interval.

Thus, by way of representative example, the further antimicrobial agent may be used after the alginate oligomer and/ or the antibiotic (e.g. macrolide antibiotic), but a preceding or simultaneous or intervening use may be beneficial in some circumstances.

The choice of anti-microbial agent will of course need to be appropriate for the location undergoing treatment, but for instance anti-microbial agents, e.g. antibiotics, antifungals, antivirals, antiseptics may be used and/or sterilising conditions such as irradiation (e.g. UV, X-ray, gamma) extremes of temperature, and extremes of pH.

Representative antibiotics include those discussed above, especially those stated as preferred. The alginate oligomers may also enhance the antibiotic effects of these further antibiotics.

Representative antiseptics include, but are not limited to chlorine bleach (sodium hypochlorite), quaternary ammonium compounds (e.g. benzalkonium chloride, cetyl trimethylammonium bromide, cetylpyridinium chloride), hydrogen peroxide, phenol compounds (e.g. TCP, Triclosan), alcohols (e.g. ethanol), Virkon™, iodine compounds (e.g. povidone-iodine), silver compounds (e.g. elemental silver nano/microparticles).

Antimicrobial surfactants are another class of antiseptics. These are compounds that disrupt microbial cell membranes and other structural components and therefore inhibit growth and/or viability of microorganisms. Antimicrobial surfactants and their use in antimicrobial compositions is well known in the art should further guidance be needed the discussion of antimicrobial surfactants in "Preservative-free and self-preserving cosmetics and drugs—Principles and practice", Ed. Kabara and Orth, Marcel Dekker, NY, N.Y., 1997, is explicitly incorporated by reference in its entirety. Antimicrobial surfactants may be anionic, cationic, non-ionic or amphoteric. Examples of antimicrobial anionic surfactants include, but are not limited to, sodium dodecyl sulfate (sodium lauryl sulfate), sodium dodecyl aminopropionic acid, sodium ricinoleate, bile acids, alkylaryl sulfonates, Grillosan DS7911, disodium undecylenic acid monoethanol amidosulfosuccinate. Examples of antimicrobial cationic surfactants include, but are not limited to, the quaternary ammionium compounds, the aminimides and chlorhexidine compounds. Examples of antimicrobial non-ionic surfactants include, but are not limited to, the monoesters of fatty acids, polyethyleneglycomonoesters of alkyldihydroxybenzoic acids, glucosamine derivatives and diethanolamides of N-lauroyl dipeptides. Examples of antimicrobial amphoteric surfactants include, but are not limited to, the alkyl betaines, the alkylamidopropylbetaines, the alkyl aminopropionates, the alkyliminodipropionates and the alkylimidazolines.

Representative antifungals include, but are not limited to the polyenes (e.g. natamycin, rimocidin, filipin, nystatin, amphotericin B, candicin; the imidazoles (e.g. miconazole, ketoconazole, clotrimazole, econazole, bifonazole, butoconazole, fenticonazole, isoconazole, oxiconazole, sertaconazole, sulconazole, tioconazole); the triazoles (e.g. fluconazole, itraconazole, isavuconazole, ravuconazole, posaconazole, voriconazole, terconazole); the allylamines (e.g. terbinafine, amorolfine, naftifine, butenafine); and the echinocandins (e.g. anidulafungin, caspofungin, micafungin).

Representative antivirals include, but are not limited to abacavir, acyclovir, adefovir, amantadine, amprenavir, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, immunovir, idoxuridine, imiquimod, indinavir, inosine, interferon type III, interferon type, II interferon type I, lamivudine, lopinavir, loviride, maraviroc, moroxydine, nelfinavir, nevirapine, nexavir, oseltamivir, penciclovir, peramivir, pleconaril, podophyllotoxin, raltegravir, ribavirin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine The further anti-microbial agent may conveniently be applied before, simultaneously with, following or between the alginate oligomer and/or the antibiotic. Conveniently the further anti-microbial agent is applied at substantially the same time as the alginate oligomer and/or the antibiotic or afterwards. For example, the further anti-microbial agent is applied at least 1 hour, preferably at least 3 hours, more preferably at least 5 and most preferably at least 6 hours after the alginate oligomer and/or the antibiotic is administered. In other embodiments the further antimicrobial may conveniently be applied or administered before the alginate oligomer and/or the antibiotic, e.g. at least 1 hour, at least 3 hours, at least 6 hours before the alginate oligomer and/or the antibiotic. In these embodiments the alginate oligomer and/or the antibiotic can be applied or administered with or without a further application of the further antimicrobial. To optimise the anti-microbial effect of the further anti-microbial agent it can be given (e.g. administered or delivered) repeatedly at time points appropriate for the agent used. The skilled person is able to devise a suitable dosage or usage regimen. In long term treatments the alginate oligomer and/or the antibiotic can also be used repeatedly. The alginate oligomer can be applied as frequently as the antibiotic and/or the further anti-microbial agent, but will typically be less frequently. The frequency required will depend on the location of the *Acinetobacter* organism, colony composition and the anti-microbial used and the skilled person is able to optimise the dosage or usage patterns to optimise results.

In an advantageous embodiment the alginate oligomer and/or the antibiotic may be used or applied after physical removal or reduction (e.g. debridement) of the *Acinetobacter*-containing colony/population causing the infection at the location undergoing treatment. The population may or may not be in a biofilm.

Following removal of, or an attempt to remove, the *Acinetobacter*-containing colony/population, the location may be contacted with the alginate oligomer for between 0 and 24 hours, particularly 2 and 12 hours, more particularly 4 and 8 hours, most particularly 5 and 7 hours, e.g. 6 hours. Following this, the antibiotic, and if desired the further anti-microbial agent, may be applied. Such a scenario may be desirable or particularly applicable in a clinical setting. In the case of *Acinetobacter* infected wounds the duration of incubation can be conveniently be designed to correspond to scheduled changes of the wound dressing.

Physical removal of the *Acinetobacter*-containing colony/population can be carried out with any suitable surgical, mechanical or chemical means. Conveniently this can be the use of a liquid, gel, gel-sol, semi-solid compositions or gas applied at pressure to the colony/population, sonication, laser, or by abrasive implement. A composition used in the removal itself or as a wash solution before, during or afterwards may conveniently contain the alginate oligomer and/or the antibiotic.

Accordingly, in one specific embodiment there is provided a debridement or wash composition e.g. solution for wounds containing an alginate oligomer, particularly any alginate oligomer as herein defined, and/or an antibiotic, e.g. a macrolide antibiotic, particularly any macrolide antibiotic as herein defined (e.g. a macrolide, preferably selected from azithromycin, clarithromycin, dirithromycin, erythromycin, roxithromycin or spiramycin), for use in the treatments and methods of the invention. Such a debridement composition will typically be a sterile solution, particularly an aqueous sterile solution or an oil-based sterile solution, and may additionally contain proteolysis enzymes (e.g. collagenase, trypsin, pepsin, elastase), an abrasive solid phase (e.g. colloidal silica, ground pumice, ground plant or animal shell).

Use of the alginate oligomers and the antibiotic in combination or conjunction with immunostimulatory agents may also be beneficial in the application of the methods of the invention in a clinical situation. These immunostimulatory agents may conveniently be used at timepoints corresponding to those described above in relation to anti-microbial agents and may optionally be used in combination with an alginate oligomer and/or the antibiotic and/or a further anti-microbial agent Suitable immunostimulatory agents include, but are not limited to cytokines e.g. TNF, IL-1, IL-6, IL-8 and immunostimulatory alginates, such as high M-content alginates as described for example in U.S. Pat. No. 5,169,840, WO91/11205 and WO03/045402 which are explicitly incorporated by reference herein in their entirety, but including any alginate with immunostimulatory properties.

Use of the alginate oligomers and the antibiotic in combination or conjunction with growth factors, e.g. PDGF, FGF, EGF, TGF, hGF and enzymes may also be beneficial in the medical uses of the invention. Representative examples of suitable enzymes include but are not limited to proteases, e.g. serine proteases, metalloproteases and cysteine proteases (examples of these types of proteases are listed in EP0590746, the entire contents of which are incorporated herein by reference); nucleases, e.g. DNase I and II, RNase A, H, I, II, III, P, PhyM, R; lipases and enzymes capable of degrading polysaccharides.

Use of the alginate oligomers and the antibiotic in combination or conjunction with a physiologically tolerable mucosal viscosity reducing agent could also be beneficial, e.g. a nucleic acid cleaving enzyme (e.g. a DNase such as DNase I), gelsolin, a thiol reducing agent, an acetylcysteine, sodium chloride, an uncharged low molecular weight polysaccharide (e.g. dextran), arginine (or other nitric oxide precursors or synthesis stimulators), or an anionic polyamino acid (e.g. poly ASP or poly GLU). Ambroxol, romhexine, carbocisteine, domiodol, eprazinone, erdosteine, letosteine, mesna, neltenexine, sobrerol, stepronin, tiopronin are specific mucolytics of note.

Use of the alginate oligomers and the antibiotic in combination or conjunction with alpha blockers may also be beneficial in the medical uses of the invention, in the treatment of chronic bacterial prostatitis especially. Representative examples of suitable alpha blockers include but are not limited to the selective alpha-1 blockers (e.g. doxazosin, dilodosin, prazosin, tamsulosin, alfuzosin, terazosin), and the non-selective adrenergic blockers (e.g. phenoxybenzamine, phentolamine).

Use of the alginate oligomers and the antibiotic in combination or conjunction with bronchodilators may also be beneficial in the medical uses of the invention, in the treatment of respiratory diseases associated with *Acinetobacter* organisms especially (which may include COPD, COAD, COAP, pneumonia, cystic fibrosis, emphysema and asthma). Representative examples of suitable bronchodilators include but are not limited to the β2 agonists (e.g. pirbuterol, epinephrine, salbutamol, salmeterol, levosalbutamol, clenbuterol), the anticholinergics (e.g. ipratropium, oxitropium, tiotropium) and theophylline.

Use of the alginate oligomers and the antibiotic in combination or conjunction with corticosteroids may also be beneficial in the medical uses of the invention, in the treatment of respiratory diseases associated with *Acinetobacter* organisms especially (which may include COPD, COAD, COAP, pneumonia, cystic fibrosis, emphysema and asthma). Representative examples of suitable corticosteroids include but are not limited to prednisone, flunisolide, triamcinolone, fluticasone, budesonide, mometasone, beclomethasone, amcinonide, budesonide, desonide, fluocinonide, fluocinolone, halcinonide, hydrocortisone, cortisone, tixocortol, prednisolone, methylprednisolone, prednisone, betamethasone, dexamethasone, fluocortolone, aclometasone, prednicarbate, clobetasone, clobetasol, and fluprednidene.

The alginate oligomers and the antibiotic can be used optionally with any other therapeutically active agent it may be desired to use, e.g. anti-microbial agent, an anti-inflammatory agent (e.g. an anti-inflammatory steroid), an immunostimulatory agent, a mucosal viscosity reducing agent, a growth inhibitor or an enzyme or an alpha blocker, a bronchodilator or a corticosteroid. The combined use of an alginate oligomer and an antibiotic with a further therapeutically active agent (e.g. an anti-microbial or anti-inflammatory agent, an immunostimulatory agent, a mucosal viscosity reducing agent, a growth inhibitor or an enzyme or an alpha blocker, a bronchodilator or a corticosteroid) may improve the clinical effects of the active agent and this may advantageously allow the dose (e.g. the usual or normal dose) of the further therapeutically active agent to be reduced e.g. it may be used at its normal or usual dose or at a lower dose, for example at up to 50% (or at 50%) of its normal dose.

In the case of medical use, the alginate oligomers and antibiotics of the invention may be administered to the subject in any convenient form or by any convenient means, e.g. by topical, oral, parenteral, enteral, parenteral routes or by inhalation. Preferably the alginate and antibiotics will be administered by topical, oral or parenteral routes or by inhalation. The alginate oligomers and antibiotics need not be in the same composition and need not be administered via the same route. In some instances it will be preferred that they are not administered via the same route.

The skilled man will be able to formulate the alginate oligomers and the antibiotics of the invention into pharmaceutical compositions that are adapted for these routes of administration according to any of the conventional methods known in the art and widely described in the literature.

The present invention therefore also provides a pharmaceutical composition for use in any of the above-mentioned methods or uses comprising an alginate oligomer as defined herein together with at least one pharmaceutically acceptable carrier, diluent or excipient. This composition may also comprise an antibiotic as defined herein.

The present invention therefore also provides a pharmaceutical composition for use in any of the above-mentioned methods or uses comprising a antibiotic, e.g. a macrolide antibiotic as defined herein together with at least one pharmaceutically acceptable carrier, diluent or excipient. This composition may also comprise an alginate oligomer as defined herein.

The active ingredient may be incorporated, optionally together with other active agents, with one or more conventional carriers, diluents and/or excipients, to produce conventional galenic preparations such as tablets, pills, powders (e.g. inhalable powders), lozenges, sachets, cachets, elixirs, suspensions, emulsions, solutions, syrups, aerosols (as a solid or in a liquid medium), sprays (e.g. nasal sprays), compositions for use in nebulisers, ointments, soft and hard gelatine capsules, suppositories, sterile injectable solutions, sterile packaged powders, and the like. Sterile inhalable compositions are of particular note for use in the treatment of respiratory diseases associated with *Acinetobacter* organisms (which may include COPD, COAD, COAP, pneumonia, cystic fibrosis, emphysema and asthma).

Examples of suitable carriers, excipients, and diluents are lactose, dextrose, sucrose, sorbitol, mannitol, starches, gum acacia, calcium phosphate, inert alginates, tragacanth, gelatine, calcium silicate, microcrystalline cellulose, polyvinylpyrrolidone, cellulose, water syrup, water, water/ethanol, water/glycol, water/polyethylene, hypertonic salt water, glycol, propylene glycol, methyl cellulose, methylhydroxybenzoates, propyl hydroxybenzoates, talc, magnesium stearate, mineral oil or fatty substances such as hard fat or suitable mixtures thereof. Excipients and diluents of note are mannitol and hypertonic salt water (saline).

The compositions may additionally include lubricating agents, wetting agents, emulsifying agents, suspending agents, preserving agents, sweetening agents, flavouring agents, and the like.

As discussed above, the alginate oligomers and the antibiotics proposed for use according to the invention may be used in combination with other therapeutic agents, for example to be administered together, in a single pharmaceutical formulation or composition, or separately (i.e. for separate, sequential or simultaneous administration). Thus, the alginate oligomers and/or the antibiotics of the invention may be combined with a further therapeutically active agent, e.g. in a pharmaceutical kit or as a combined ("combination") product.

Thus a further aspect of the present invention provides a product containing an alginate oligomer and/or an antibiotic, e.g. a macrolide antibiotic, as defined herein and a further active agent as a combined preparation for separate, simultaneous or sequential use (e.g. application to a *Acinetobacter* organism and/or administration to a subject or location) for inhibiting the growth and/or viability of *Acinetobacter* organisms, combating *Acinetobacter* contamination of a location, combating a population of *Acinetobacter* organisms and, in particular, the treatment of an *Acinetobacter* infection in a subject.

Additional therapeutically active agents may be included in the pharmaceutical compositions, as discussed above in relation to combination therapies above.

The invention also provides products (e.g. a pharmaceutical kit or a combined ("combination") product) or compositions (e.g. a pharmaceutical composition) wherein the product or composition comprises an alginate oligomer as herein defined and an antibiotic, e.g. selected from the group azithromycin, clarithromycin, dirithromycin, erythromycin, troleandomycin, aztreonam, imipenem, meropenem, ertapenem, doripenem, panipenem/betamipron, biapenem, PZ-601, cefixime, cefdinir, cefditoren, cefoperazone, cefotaxime, cefpodoxime, ceftazidime, ceftibuten, ceftizoxime, ceftriaxone, cefepime, demeclocycline, doxycycline, minocycline, oxytetracycline, tetracycline, bacitracin, colistin, polymyxin B, ciprofloxacin, enoxacin, gatifloxacin, levofloxacin, lomefloxacin, moxifloxacin, norfloxacin, ofloxacin, and trovafloxacin. Preferably the antibiotic is selected from the group ceftazidime, imipenem/cilastatin, meropenem, aztreonam, oxytetracycline, colistin, azithromycin and ciprofloxacin, preferably it is azithromycin. For example, the antibiotic may be selected from amikacin, gentamicin, kanamycin, neomycin, netilmicin, streptomycin, tobramycin, azithromycin, clarithromycin, dirithromycin, erythromycin, roxithromycin, telithromycin, CarbomycinA, josamycin, kitasamycin, midecamicine, oleandomycin, spiramycin, tylosin, troleandomycin, aztreonam, imipenem, meropenem, ertapenem, doripenem, panipenem/betamipron, biapenem, PZ-601, cefixime, cefdinir, cefditoren, cefoperazone, cefotaxime, cefpodoxime, ceftazidime, ceftibuten, ceftizoxime, ceftriaxone, cefepime, demeclocycline, doxycycline, minocycline, oxytetracycline, tetracycline, bacitracin, colistin, polymyxin B, ciprofloxacin, enoxacin, gatifloxacin, levofloxacin, lomefloxacin, moxifloxacin, norfloxacin, ofloxacin, and trovafloxacin. In particular, the antibiotic may selected from ceftazidime, imipenem/cilastatin, meropenem, aztreonam, oxytetracycline, azithromycin, clarithromycin, dirithromycin, erythromycin, roxithromycin, spiramycin and ciprofloxacin, and it is particularly preferred that the antibiotic is selected from ceftazidime, imipenem/cilastatin, meropenem, aztreonam, azithromycin, clarithromycin, dirithromycin, erythromycin, roxithromycin, spiramycin and ciprofloxacin. More preferably the antibiotic is selected from aztreonam, azithromycin, clarithromycin, dirithromycin, erythromycin, roxithromycin, spiramycin and ciprofloxacin. In other embodiments the antibiotic used is not tobramycin, amikacin and/or colistin. In other embodiments the antibiotic used is not an aminoglycoside or a polypeptide antibiotic. In other embodiments the antibiotic used is not an antibiotic that has a positive charge under the conditions in which it will be used with the alginate oligomer, e.g. antibiotics with at least 3, e.g. at least 4, 5, 6 or 7 amino (—NH2) groups.

In preferred embodiments the product or composition comprises an alginate oligomer as herein defined and a macrolide antibiotic, e.g. selected from the group azithromycin, clarithromycin, dirithromycin, erythromycin, roxithromycin, telithromycin, CarbomycinA, josamycin, kitasamycin, midecamicine, oleandomycin, spiramycin, troleandromycin, tylosin. Preferably the macrolide antibiotic is an azalide macrolide, preferably azithromycin.

These products and compositions are specifically contemplated as for use in the methods of the invention. The products and compositions can be pharmaceutical or non-pharmaceutical. Therefore the products and compositions of this aspect of the invention can be used in any of the methods of the invention.

The use of alginate oligomers as herein defined to manufacture such pharmaceutical products and pharmaceutical compositions for use in the medical methods of the invention is also contemplated.

Further active agents may also be incorporated. The above and following discussion of additional active agents and excipients and the like is directly applicable in its entirety to this aspect of the invention.

In some instances it may be beneficial to administer the alginate oligomers and/or the antibiotics as defined herein to animals, e.g. to promote weight gain/growth. Administration can be achieved in the form of the pharmaceutical compositions described above, but conveniently the alginate oligomers and/or the antibiotics as defined herein may be used as a conventional feed additive, i.e. a product that is added to animal feed in small, nutritionally inconsequential amounts. The use of feed additives in animal feeds is well established and it would be entirely routine for a skilled man to determine and use appropriate amounts of the alginates of the invention to achieve the desired effects, e.g. weight gain/growth.

The relative content of the alginate oligomer and the antibiotic can vary depending on the dosage required and the dosage regime being followed and this will depend on the subject to be treated and the location and identity of the *Acinetobacter*, and/or the constituents of the *Acinetobacter* contamination or *Acinetobacter*-containing population. Preferably, the composition will comprise an amount of alginate oligomer that will provide a measurable increase in the effectiveness of the antibiotic to inhibit the growth and/or viability of the *Acinetobacter* organisms, e.g. an amount of alginate oligomer that will at least double, at least quadruple, at least octuple, at least sexdecuple or at least duotrigecuple the effectiveness of the macrolide antibiotic to inhibit the growth and/or viability of the *Acinetobacter* organisms. Put in a different way, the composition will comprise an amount of alginate oligomer and an amount of antibiotic that will provide a measurable treatment of the infection being targeted.

Preferably the composition or product will comprise sufficient alginate oligomer that upon administration to a subject or application to a location, the local concentration of the oligomer will be at least 2%, preferably at least 4%, 6% or 8% and most preferably at least 10% (weight by volume). The antibiotic preferably will be present in an amount that is sufficient to provide a local concentration of at least 0.03125 µg/ml, preferably at least 0.0625, 0.125, 0.25, 0.5, 1, 2, 4, 8, 16, 32, 64, 128, 256, 512, 1024, 2048 or 4096 µg/ml. The skilled man would know that the amounts of alginate oligomer and/or antibiotic can be reduced if a multiple dosing regime is followed or increased to minimise the number of administrations or applications.

The compositions and products of this aspect will typically comprise between 1% and 99%, 5% and 95%, 10% and 90% or 25% and 75% alginate oligomer and 1% and 99%, 5% and 95%, 10% and 90% or 25% and 75% macrolide antibiotic, allowance being made for other ingredients.

Parenterally administrable forms, e.g., intravenous solutions, should be sterile and free from physiologically unacceptable agents, and should have low osmolarity to minimize irritation or other adverse effects upon administration and thus solutions should preferably be isotonic or slightly hypertonic, e.g. hypertonic salt water (saline). Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405-1412 and 1461-1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the biopolymers and which will not interfere with the manufacture, storage or use of products.

For topical administration the alginate oligomer and/or the antibiotic can be incorporated into creams, ointments, gels, transdermal patches and the like. The alginate oligomers and/or the antibiotic can also be incorporated into medical dressings, for example wound dressings e.g. woven (e.g. fabric) dressings or non-woven dressings (e.g. gels or dressings with a gel component). The use of alginate polymers in dressings is known, and such dressings, or indeed any dressings, may further incorporate the alginate oligomers of the invention.

Accordingly, in a further specific embodiment, the invention further provides a wound dressing comprising an alginate. oligomer (which may be any alginate oligomer as herein defined) and/or an antibiotic, e.g. a macrolide antibiotic, (which may be any antibiotic or macrolide antibiotic as herein defined) for use, where appropriate, in the treatments and methods of the invention.

Further topical systems that are envisaged to be suitable are in situ drug delivery systems, for example gels where solid, semi-solid, amorphous or liquid crystalline gel matrices are formed in situ and which may comprise the alginate oligomer and/or the antibiotic. Such matrices can conveniently be designed to control the release of the alginate oligomer and/or the antibiotic from the matrix, e.g. release can be delayed and/or sustained over a chosen period of time. Such systems may form gels only upon contact with biological tissues or fluids. Typically the gels are bioadhesive. Delivery to any body site that can retain or be adapted to retain the pre-gel composition can be targeted by such a delivery technique. Such systems are described in WO 2005/023176.

For application to oral, buccal and dental surfaces, toothpastes, dental gels, dental foams and mouthwashes are mentioned specifically. Thus, in one particular aspect is included an oral health care, or oral hygiene, composition, comprising an alginate oligomer and an antibiotic (which may be any alginate oligomer or antibiotic as defined herein), particularly a mouthwash, toothpaste, dental gel or dental foam for use, where appropriate, in the treatments and methods of the invention.

Inhalable compositions are also of note. The formulation of compositions suitable for inhalation is routine for the skilled man and has long been standard practice in the treatment of respiratory diseases. Inhalable compositions may, for instance, take the form of inhalable powders, solutions or suspensions. The skilled man would be able to select the most appropriate type of delivery system for his needs and be able to prepare suitable formulations of the alginates and/or antibiotics of the invention for use in that system. Propellant-free nebulisable solutions and inhalable powder formulations are particularly preferred.

As noted above, a preferred composition of the invention is a debridement composition that is used in a debridement process to remove an colony or population of *Acinetobacter* organisms, for example from a tissue. Typically such a composition will be liquid, but gels, gel-sols, or semi-solid compositions might be used. The composition might be used to debride the colony/population (e.g. by application to the tissue under pressure) and/or may be used to bathe the tissue before, during and/or after debridement by other means such as by surgical, mechanical or chemical processes. The skilled person is readily able to formulate debridement compositions in accordance with the invention.

In the case of *Acinetobacter* organisms on an inanimate surface on in an inanimate material, the alginate oligomer and/or antibiotic may be applied to the surface or material to be treated in any convenient composition or formulation, or by any convenient means. Thus the alginate oligomer and/or antibiotic may be in liquid, gel, gel-sol, semi-solid or solid form (e.g. solutions, suspensions, homogenates, emulsions, pastes, powders, aerosols, vapours). Typically the compositions for treating such inanimate surfaces or materials will be a non-pharmaceutically acceptable composition. The choice of composition form will be dictated by the identity of the *Acinetobacter* organism on the surface or in the material and location of the surface or material. For instance, if the location is a fluid line it might be convenient to apply a fluid composition. It might also be preferred to use a composition that persists on the surface or in the part of the fluid line to be treated but that will not leach into the fluid of normal use, e.g. an adhesive gel. The skilled person is readily able to prepare suitable compositions from his common general knowledge. For instance, the alginate oligomer and/or antibiotic may be added to a paint formulation and applied to the surface to be treated, e.g. a boat hull or other part of a boat's structure that is exposed to water, or to a building or any part thereof, a tank (e.g. a storage or processing tank) or indeed to any part of any industrial machinery. Such compositions may conveniently also comprise a further anti-microbial agent, as described above, e.g. an antibiotic, chlorine bleach, TCP, ethanol, Virkon™, povidone-iodine, silver compounds, antimicrobial surfactants etc. As the compositions need not be pharmaceutically acceptable, harsher antimicrobials can be used subject to considerations of surface damage, environmental contamination, user safety and contamination of the treated surface and interaction with the other components of the composition.

The compositions of the invention may be formulated so as to provide quick, sustained or delayed release of the active ingredient after administration to the subject/surface by employing procedures well known in the art. Adhesive compositions are also preferred. Adhesive, sustained and/or delayed release formulations may be particularly convenient.

In a further aspect the invention provides products susceptible to contamination/colonisation by *Acinetobacter* organisms whose susceptible surfaces have been pretreated with an alginate oligomer and/or an antibiotic, e.g. a macrolide antibiotic, as defined herein.

By "pretreated" it is meant that the susceptible surface is exposed to an alginate oligomer and/or an antibiotic prior to an exposure to an *Acinetobacter* organism and that the alginate oligomer and/or antibiotic persists on the surface for a duration sufficient to prevent contamination/colonisation by an *Acinetobacter* organism for an appreciable duration of time. Preferably the alginate oligomer and/or the antibiotic will persist for substantially the useful life of the surface, e.g. the pretreatment results in a substantially permanent coating of an alginate oligomer and/or an antibiotic. Thus a pretreated surface/product is one to which the alginate olgimer and/or antibiotic is applied and on which it remains. Such a product/surface may be a coated product/surface.

Non-limiting examples of products and surfaces susceptible to *Acinetobacter* contamination/colonisation by *Acinetobacter* organisms are described above. Particular mention may be made of medical and surgical devices (e.g. endotracheal or tracheostomy tubes) and food or drink processing, storage or dispensing equipment.

Pretreatment can be achieved by any convenient means, for example any form of applying the alginate oligomer and antibiotic to the surface, notably coating the surface, e.g. spray drying, polymer coating with a polymer incorporating the alginate oligomer and/or antibiotic, and painting, varnishing or lacquering with paint, varnish or lacquer formulations containing the alginate oligomer and/or antibiotic. Such a "coating" composition (e.g. a paint, varnish or lacquer) containing an alginate oligomer and/or antibiotic represents a further aspect of the present invention. Alternatively, the alginate oligomer and antibiotic can be incorporated into the material from which the object or its susceptible parts are manufactured. This approach is suited to objects, or constituent parts thereof, manufactured from polymers such as plastics and silicones, e.g. the medical and surgical devices described above. This may include any kind of line, including catheters (e.g. central venous and urinary catheters), prosthetic devices e.g., heart valves, artificial joints, false teeth, dental crowns, dental caps and soft tissue implants (e.g. breast, buttock and lip implants). Any kind of implantable (or "in-dwelling") medical device is included (e.g. stents, intrauterine devices, pacemakers, intubation tubes (e.g. endotracheal or tracheostomy tubes), prostheses or prosthetic devices, lines or catheters). Further products include food processing, storage, dispensing or preparation equipment or surfaces, tanks, conveyors, floors, drains, coolers, freezers, equipment surfaces, walls, valves, belts, pipes, air conditioning conduits, cooling apparatus, food or drink dispensing lines, heat exchangers, boat hulls or any part of a boat's structure that is exposed to water, dental waterlines, oil drilling conduits, contact lenses and storage cases.

The invention will be further described with reference to the following non-limiting Examples.

EXAMPLES

Example 1

Effect of G-Fragment Alginate Oligomers on Minimum Inhibitory Concentrations of Ceftazidime or Ciprofloxacin in Combination with Different Concentrations of Azithromycin Bacterial Strains:
Multidrug resistant *Acinetobacter* baumannii isolated from a source in Libya
*Staphylococcus aureus* NCTC 6571 MIC CONTROL STRAIN (Oxford Staph.)
Chemicals and Bacterial Media:
Following retrieval from −80° C. storage, bacterial colonies were grown on blood agar with 5% sheep blood and were used to inoculate tryptone soya broth (TSB) for overnight growth. Antibiotics were diluted in cation-adjusted Mueller-Hinton broth (CAMHB) or CAMHB with G-fragments (Oligo CF-5/20 90-95% G residues) at 2%, 6% or 10%. Antibiotics were pharmaceutical grade purchased from Sigma-Aldrich. OligoG CF-5/20 G-fragments were provided by Algipharma.
Minimum Inhibitory Concentration Assay (Jorgensen et al., Manual of Clinical Microbiology, 7th ed. Washington, D.C.: American Society for Microbiology, 1999; 1526-43:

Overnight bacterial cultures as described above were diluted in sterile water until the OD625 was between 0.08 and 0.10 to confirm that the cell density was equivalent to 0.5 McFarland standard.

Two-fold ciprofloxacin and two-fold ceftazidime serial dilutions were prepared in CAMHB or CAMHB supplemented with azithromycin at either 4 µg/ml or 8 µg/ml and G-fragments (Oligo CF-5/20 90-95% G residues) at 0%, 2%, 6% or 10% and were placed in duplicate wells of flat-bottom 96-well microtiter plates (100 µl in each well). Ceftazidime was used at 0-1024 µg ml$^{-1}$ and Ciprofloxacin was used at 0-256 µg ml$^{-1}$.

Bacterial cultures at 0.5 McFarland standard were diluted ten-fold in CAMHB and 5 µl added to the microtiter plates containing the antibiotic serial dilutions. Plates were wrapped in parafilm and incubated at 37° C. for 16-20 hours. MIC values for each antibiotic were determined as the lowest concentration at which there was no visible growth. Results are shown in Table 1

TABLE 1

| | | Antibiotic and MIC value µg/ml | | | |
|---|---|---|---|---|---|
| Strain | % G | Ceftazidime with azithromycin at 4 µg/ml | Ceftazidime with azithromycin at 8 µg/ml | Ciprofloxacin with azithromycin at 4 µg/ml | Ciprofloxacin with azithromycin at 8 µg/ml |
| A. bau | 0 G | 1024 | 512 | 128 | 128 |
| | +2% G | <4 µg/ml Az | <8 µg/ml Az | 64 Cpr, 4 Az | <8 µg/ml Az |
| | +6% G | <4 µg/ml Az | <8 µg/ml Az | <4 µg/ml Az | <8 µg/ml Az |
| | +10% G | <4 µg/ml Az | <8 µg/ml Az | <4 µg/ml Az | <8 µg/ml Az |
| S. Aur | 0 G | <4 µg/ml Az | <8 µg/ml Az | <4 µg/ml Az | <8 µg/ml Az |
| | +2% G | <4 µg/ml Az | <8 µg/ml Az | <4 µg/ml Az | <8 µg/ml Az |
| | +6% G | <4 µg/ml Az | <8 µg/ml Az | <4 µg/ml Az | <8 µg/ml Az |
| | +10% G | <4 µg/ml Az | <8 µg/ml Az | <4 µg/ml Az | <8 µg/ml Az |

These data show that the growth of this strain of *Acinetobacter baumannii* could be completely inhibited by a combination of 4 μg/ml azithromycin and 2% or more G-fragments. In the absence of G-fragments, azithromycin at 4 μg/ml and at 8 μg/ml was not capable of inhibiting growth and inhibition was only achieved by the addition of an additional antibiotic (ceftazidime or ciprofloxacin).

It can be concluded that alginate oligomers (e.g. G-fragments) enhance the efficacy of azithromycin against *Acinetobacter baumannii* and in particular alginate oligomers (e.g. G-fragments) enhance the effectiveness of azithromycin to inhibit growth of *Acinetobacter baumannii*. The use of azithromycin together with alginate oligomers (e.g. G-fragments) is therefore predicted to constitute a highly effective treatment for *Acinetobacter* infections and contamination.

Example 2

The study of Example 1 was repeated using azithromycin at 1 or 2 μg/ml and on an MDR strain of *Pseudomonas aeruginosa*. Results are shown in Table 2.

TABLE 2

Minimum inhibitory concentrations (MICs) of two antibiotics in combination with each other (azithromycin with either ceftazidime or ciprofloxacin) for multi drug resistant (MDR) strains of *Pseudomonas aeruginosa* and *Acinetobacter baumannii* in the presence of varying concentrations of OligoCF-5/20 (0-10%)
(MIC values are expressed in μg ml$^{-1}$).

| Antibiotic | | V1*<br>MDR R22 PA<br>(China) | V4*<br>ACB (Libya) |
|---|---|---|---|
| Ceftazidime with azithromycin at 8 μg/ml | 0 G | 256 | 512 |
| | +2% G | 128 | 8 μg/ml Az |
| | +6% G | 32 | 8 μg/ml Az |
| | +10% G | 16 | 8 μg/ml Az |
| Ceftazidime with azithromycin at 4 μg/ml | 0 G | 128 | 1024 |
| | +2% G | 128 | 4 μg/ml Az |
| | +6% G | 64 | 4 μg/ml Az |
| | +10% G | 8 | 4 μg/ml Az |
| Ceftazidime with azithromycin at 2 μg/ml | 0 G | 128 | 1024 |
| | +2% G | 64 | 256 |
| | +6% G | 32 | 2 |
| | +10% G | 16 | ≤1 Cf |
| Ceftazidime with azithromycin at 1 μg/ml | 0 G | 128 | 1024 |
| | +2% G | 64 | 512 |
| | +6% G | 16 | 128 |
| | +10% G | 16 | ≤1 Cf |

TABLE 2-continued

Minimum inhibitory concentrations (MICs) of two antibiotics in combination with each other (azithromycin with either ceftazidime or ciprofloxacin) for multi drug resistant (MDR) strains of *Pseudomonas aeruginosa* and *Acinetobacter baumannii* in the presence of varying concentrations of OligoCF-5/20 (0-10%)
(MIC values are expressed in μg ml$^{-1}$).

| Ciprofloxacin with azithromycin at 8 μg/ml | 0 G | 16 | 128 |
|---|---|---|---|
| | +2% G | 16 | 8 μg/ml Az |
| | +6% G | 16 | 8 μg/ml Az |
| | +10% G | 8 μg/ml Az | 8 μg/ml Az |
| Ciprofloxacin with azithromycin at 4 μg/ml | 0 G | 16 | 128 |
| | +2% G | 16 | 64 Cpr |
| | +6% G | 8 | 4 μg/ml Az |
| | +10% G | 4 | 4 μg/ml Az |
| Ciprofloxacin with azithromycin at 2 μg/ml | 0 G | 32 | 128 |
| | +2% G | 16 | ≤0.25 Cpr |
| | +6% G | 16 | ≤0.25 Cpr |
| | +10% G | 8 | ≤0.25 Cpr |
| Ciprofloxacin with azithromycin at 1 μg/ml | 0 G | 16 | 64 |
| | +2% G | 16 | 32 |
| | +6% G | 8 | ≤0.25 Cpr |
| | +10% G | 8 | ≤0.25 Cpr |

■ Indicates increasing MIC values with increase in G-fragment concentration

▦ Indicates decreasing MIC values with increase in G-fragment concentration

These data show that the MIC values for ciprofloxacin and ceftazidime are greatly reduced by OligoCF-5/20 in the *Acinetobacter* organism, although there is some reduction in the MIC values seen in the *Pseudomonas* organism. As discussed in Example 1, in almost all of the experiments using higher levels of azithromycin (i.e. 8 or 4 μg/ml), the presence of OligoCF-5/20 resulted in complete inhibition of *Acinetobacter* growth without addition of ciprofloxacin or ceftazidime and thus it can be seen that OligoCF-5/20 also greatly reduces the MIC value for azithromycin in the *Acinetobacter* organism.

Example 3

Effect of G-Fragment Alginate Oligomers on Minimum Inhibitory Concentrations of Various Antibiotics and Acinetobacter Strains MIC assays as described in Example 1 were conducted using the following *Acinetobacter* strains, antibiotics and concentrations of OligoCF-5/20 as described in Tables 3 and 4.

Non-MDR Strains
  V19* 7789 *Acinetobacter baumannii*
  V20* 8065 *Acinetobacter Iwoffii*

MDR Strains
  V4* MDR ACB (Libya) *Acinetobacter baumannii*
  V9* (Egypt) *Acinetobacter baumannii*
  V10* (Egypt) *Acinetobacter Iwoffii*
  V22* 6056 *Acinetobacter Iwoffii*

TABLE 3

Minimum inhibitory concentration (MICs) of different antibiotics in different strains of *Acinetobacter baumannii* and *Acinetobacter lwoffii* in the presence of varying concentrations of OligoCF-5/20 (0-10%). (MIC values are expressed in µg ml−1).

| Antibiotic and MIC value µg/ml | % G | V22 MDR *Acin. lwoff* | V9 MDR *Acin. baum* | V19 non MDR *Acin. baum* | V10 MDR *Acin. lwoff* | V4 MDR *Acin. baum* |
|---|---|---|---|---|---|---|
| Oxytetracycline | 0 G | 2 | 2 | >256 | 0.5 | ND |
| | +2% G | 2 | 2 | >256 | 0.5 | ND |
| | +6% G | 2 | 1 | >256 | 0.5 | ND |
| | +10% G | 8 | 4 | >256 | 0.25 | ND |
| AZACTAM (Aztreonam) | 0 G | 256 | >512 | 64 | 32 | 1024 |
| | +2% G | 128 | 512 | 32 | 16 | 512 |
| | +6% G | 64 | 256 | 16 | 4 | 256 |
| | +10% G | 32 | 128 | 4 | 1 | 128 |
| Ciprofloxacin | 0 G | <0.25 | 64 | 128 | 0.5 | 64 |
| | +2% G | <0.25 | 32 | 64 | 0.5 | 32 |
| | +6% G | <0.25 | 32 | 32 | 0.25 | 16 |
| | +10% G | <0.25 | 32 | 32 | 0.25 | 16 |
| PRIMAXIN (Imipenem/ Cilastatin | 0 G | 8 | 1 | <0.5 | <0.5 | ND |
| | +2% G | 8 | 2 | <0.5 | <0.5 | ND |
| | +6% G | 8 | <0.5 | <0.5 | <0.5 | ND |
| | +10% G | 4 | <0.5 | <0.5 | <0.5 | ND |
| Meropenem | 0 G | 256 | 16 | 8 | 1 | ND |
| | +2% G | 128 | 8 | 8 | 0.5 | ND |
| | +6% G | 128 | 8 | 4 | <0.25 | ND |
| | +10% G | 64 | 4 | 0.5 | <0.25 | ND |
| Ceftazidime | 0 G | 16 | >512 | 128 | 2 | 512 |
| | +2% G | 16 | 512 | 64 | 2 | 512 |
| | +6% G | 4 | 512 | 32 | <0.5 | 512 |
| | +10% G | 2 | 256 | 32 | <0.5 | 256 |
| Azithromycin | 0 G | <0.25 | 16 | 32 | <0.25 | ND |
| | +2% G | <0.25 | 4 | 8 | <0.25 | ND |
| | +6% G | <0.25 | 0.5 | 1 | <0.25 | ND |
| | +10% G | <0.25 | <0.25 | <0.25 | <0.25 | ND |
| Erythromycin | 0 G | <0.5 | 8 | 16 | <0.5 | 8 |
| | +2% G | <0.5 | 4 | 8 | <0.5 | 2 |
| | +6% G | <0.5 | 1 | 2 | <0.5 | ≤1 |
| | +10% G | <0.5 | <0.5 | <0.5 | <0.5 | ≤1 |
| Clarithromycin | 0 G | — | 16 | 64 | <0.5 | 8 |
| | +2% G | — | 4 | 32 | <0.5 | 4 |
| | +6% G | — | 2 | 4 | <0.5 | ≤1* |
| | +10% G | — | 1 | <0.5 | <0.5 | ≤1* |
| Spiramycin | 0 G | <4 | 256 | 512 | <4 | 512 |
| | +2% G | <4 | 64 | 256 | <4 | 64 |
| | +6% G | <4 | 32 | 64 | <4 | 64 |
| | +10% G | <4 | 16 | 64 | <4 | 32 |

▒▒ Indicates increasing MIC values with increase in G-fragment concentration

░░ Indicates decreasing MIC values with increase in G-fragment concentration

Further MIC assays were conducted with the various strains and antibiotics recited in Table 4 using the following protocol.

G-block alginates (OligoG CF-5/20) were dissolved in Mueller-Hinton broth (Lab M limited, LAB114 Mueller-Hinton broth) to 1.25 times of the desired assay concentrations (2, 6 and 10%). Antibiotics were dissolved in Mueller-Hinton broth and Mueller-Hinton broth with G-block alginate at a concentration of 1.25 times the highest desired assay concentrations. Antibiotics were pharmaceutical grade purchased from Sigma-Aldrich. OligoG CF-5/20 G-fragments were provided by Algipharma AS, Norway.

Two-fold serial dilutions of antibiotics were made in Mueller-Hinton with different concentrations of G-block alginate, and the solutions were placed in four parallel wells in Nunc 384-well micro plates (30 µl per well in Nunc 242757 microplates). A group of 8 wells with no addition of antibiotics for each G-block concentration was included on each micro plate as growth reference.

Frozen stock cultures were made from overnight cultures in TSB-broth for all strains by addition of glycerol to 15% concentration prior to freezing at −80° C. At the day of analysis, overnight TSB cultures (6 ml in 50 ml tube tilted to 45-degrees angle, 200 rpm, 2.5 cm amplitude, 37° C.) were diluted in TSB until the OD600 was 0.10, and further diluted 1:40 in Mueller-Hinton broth. Each well in the 384-well assay plates was inoculated with 7.5 µl of the diluted culture. The microplates were placed in plastic bags and incubated at 37° C. The optical density at 600 nm in the microwells was measured after approximately 18 hours of incubation, and the relative growth yield in each well was calculated based on the growth in the reference groups. The MIC value was set to the highest concentration giving less than 30% growth in all 4 parallel wells within the sample groups. The microplates were further incubated for 8 hours, and optical density in the cultures was measured once more for confirmation of the estimated MIC-values.

In Table 4 there is a main table of basic data, and a secondary table which is a representation of the overall effect of the OligoCF-5/20 on the MIC value for each particular *Acinetobacter* and antibiotic combination. In the secondary table a dark shaded box represents an overall reduction in the MIC value; a hatched boxed represents an overall increase in the MIC value; M indicates that all of the MIC values were greater than the maximum concentration of antibiotic used; L indicates that all of the MIC values were less than the minimum concentration of antibiotic used; NE indicates no effect on the MIC values was observed.

TABLE 4

Minimum inhibitory concentration (MICs) of different antibiotics in different strains of *Acinetobacter baumannii* and of *Acinetobacter lwoffii* in the presence of varying concentrations of OligoCF-5/20 (0-10%). (MIC values are expressed in µg ml−1).

| Strain | G-Block | Azithromycin | Erythromycin | Roxithromycin | Dirithromycin | Aztreonam | Ceftazidime | Imipenem | Ciprofloxacin | Oxytetracycline |
|---|---|---|---|---|---|---|---|---|---|---|
| *Acinetobacter baumannii* (7789 V19) non-MDR | 0% | 8 | 8 | 16 | 32 | >16 | >16 | 0.125 | >8 | >128 |
| | 2% | <1 | 4 | 8 | 8 | 16 | >16 | 0.25 | >8 | >128 |
| | 6% | <1 | 2 | 2 | 4 | 8 | >16 | 1 | >8 | >128 |
| | 10% | <1 | 1 | 4 | 1 | 4 | >16 | 1 | >8 | >128 |
| *Acinetobacter lwoffii* (6056 V22) MDR | 0% | <2 | <2 | 4 | <2 | 64 | 8 | 2 | <2 | <2 |
| | 2% | <2 | <2 | <2 | <2 | 32 | 4 | 2 | <2 | <2 |
| | 6% | <2 | <2 | <2 | <2 | 16 | 2 | 2 | <2 | <2 |
| | 10% | <2 | <2 | <2 | <2 | 4 | 2 | <2 | <2 | <2 |
| *Acinetobacter lwoffii* (8065 V20) non-MDR | 0% | <0.13 | <1 | <1 | <1 | 2 | 0.5 | <0.031 | 0.031 | <0.25 |
| | 2% | <0.13 | <1 | <1 | <1 | 0.25 | 0.063 | <0.031 | 0.015 | <0.25 |
| | 6% | <0.13 | <1 | <1 | <1 | 0.125 | 0.031 | <0.031 | <0.015 | 0.25 |
| | 10% | <0.13 | <1 | <1 | <1 | 0.063 | 0.031 | <0.031 | <0.015 | <0.25 |
| *Acinetobacter baumannii* (Egypt V9) MDR | 0% | 4 | 8 | 8 | 4 | >16 | >16 | 2 | >8 | 1 |
| | 2% | <1 | 2 | 4 | <1 | >16 | >16 | <2 | >8 | 0.5 |
| | 6% | <1 | 1 | 4 | <1 | >16 | >16 | 2 | 8 | 1 |
| | 10% | <1 | <1 | 2 | <1 | >16 | >16 | <2 | 8 | 0.5 |
| *Acinetobacter baumannii* (MDR ACB Libya V4) | 0% | 16 | 32 | 128 | 64 | 4 | 16 | 2 | 4 | 2 |
| | 2% | 2 | 8 | 32 | 8 | 4 | 8 | 2 | 1 | 2 |
| | 6% | <1 | 4 | 16 | 2 | 1 | 8 | 2 | 1 | 2 |
| | 10% | <1 | 2 | 16 | <1 | 0.5 | 8 | <2 | 0.5 | 1 |
| *Acinetobacter lwoffii* (Egypt V10) MDR | 0% | <1 | 1 | 4 | <1 | 8 | 2 | <2 | 0.063 | 0.5 |
| | 2% | <1 | <1 | <1 | <1 | 4 | 1 | <2 | 0.031 | 0.5 |
| | 6% | <1 | <1 | <1 | <1 | 2 | 0.25 | <2 | 0.031 | 0.5 |
| | 10% | <1 | <1 | <1 | <1 | 1 | 0.25 | <2 | 0.031 | 0.5 |

TABLE 4-continued

Minimum inhibitory concentration (MICs) of different antibiotics in different strains of *Acinetobacter baumannii* and of *Acinetobacter lwoffii* in the presence of varying concentrations of OligoCF-5/20 (0-10%). (MIC values are expressed in μg ml−1).

The data presented in Tables 3 and 4 generally show that increasing concentrations of OligoCF-5/20 (0-10%) decreases MIC values for all antibiotics tested (azithromycin, erythromycin, roxithromycin, dirithromycin, clarithromycin and spiramycin (macrolides) aztreonam (monobactam) ceftazidime (cephalosporin) imipenem (carbapenem), meropenem (carbapenem), ciprofloxacin (quinolone) and oxytetracycline (tetracycline)) in one *Acinetobacter* strain or another. In almost every case where the strain being tested was not completely susceptible to the antibiotic under test (i.e. growth inhibition was seen at the lowest concentration of antibiotic tested) reduction in MIC values was seen. In Table 4, strain V9 shows M (MICs were above the maximum concentration of antibiotic used) when aztreonam or ceftazidime are used. However, in Table 3, these antibiotics show reduced MIC values with increasing concentrations of OligoCF-5/20 in strain V9. Similarly, in Table 4, strain V19 shows M (MICs were above the maximum concentration of antibiotic used) when ciprofloxacin or ceftazidime are used However, in Table 3, these antibiotics show reduced MIC values with increasing concentrations of OligoCF-5/20 in strain V9. In Table 4 the MIC values of imipenem in strain V19 were increased by increasing concentrations of OligoCF-5/20, However, increasing concentrations of OligoCF-5/20 had no effect on MIC values of imipenem in this strain according to the data of Table 3. Overall, the effectiveness of oxytetracycline was least influenced by increasing concentrations of OligoCF-5/20, however, oxytetracycline still showed decreased MIC values in two of the tested strains V10 (Table 3) and V4 (Table 4).

These data highlight the ability of alginate oligomers to enhance the effectiveness of antibiotics against *Acinetobacter* organisms and, more particularly, the ability of alginate oligomers to overcome the resistance these bacteria may have to antibiotics.

Potentiation of MICs for *Acinetobacter* strains was found to be most pronounced with the macrolides, but significant reduction of MIC values was also seen with β-lactams. Importantly, the reduction in MIC value may be such as to change a phenotype from resistant to sensitive.

Example 4

Effect of M-Block Alginate Oligomers on Minimum Inhibitory Concentrations of Aztreonam, Ciprofloxacin, Meropenem and Azithromycin in two *Acinetobacter* strains The study described in Example 1 was repeated with the following strains of *Acinetobacter baumannii*, antibiotics and M-block alginate oligomer in place of OligoG CF-5/20 as detailed in Table 5. The M-block oligomer is 100% M with a DPn of 15 to 18.

TABLE 5

Minimum inhibitory concentration (MICs) of different antibiotics for two strains of *Acinetobacter baumannii* displaying an MDR phenotype in the presence of varying concentrations of M-block oligomer (0-10%). (MIC values are expressed in μg ml$^{-1}$).

| Strain → Antibiotic and MIC value μg/ml | M block concentration | V4 MDR *Acin baum* (Libya) | V19 non MDR *Acin. baum* |
|---|---|---|---|
| Aztreonam | 0 M | 2048 | 64 |
|  | +2% M | 512 | 32 |
|  | +6% M | 256 | 8 |
|  | +10% M | 64 | 8 |
| Ciprofloxacin | 0 M | 64 | 64 |
|  | +2% M | 64 | 32 |
|  | +6% M | 64 | 16 |
|  | +10% M | 128 | 128 |
| Meropenem | 0 M | 16 | 8 |
|  | +2% M | 32 | 4 |
|  | +6% M | 16 | 2 |
|  | +10% M | 8 | 1 |
| Azithromycin | 0 M | 8 | 32 |
|  | +2% M | 8 | 16 |
|  | +6% M | 8 | 16 |
|  | +10% M | 2 | 16 |

▒ Indicates decreasing MIC values with increase in G-fragment concentration

▒ Indicates increasing MIC values with increase in G-fragment concentration

The results displayed in Table 5 show that M-block oligomers are, like OligoG CF-5/20, also effective in lowering MIC values for a number of different antibiotics (including a macrolide) in MDR and non-MDR strains of *Acinetobacter baumannii*.

The invention claimed is:

1. A method of reducing *Acinetobacter*, said method comprising contacting said *Acinetobacter* with an antibiotic together with an alginate oligomer, wherein the antibiotic is selected from the group consisting of a macrolide, a β-lactam, a tetracycline, and a quinolone.

2. The method of claim 1, said method comprising administering to a subject infected, suspected to be infected, or at risk of infection with *Acinetobacter*, an effective amount of said antibiotic together with said alginate oligomer.

3. The method of claim 2 comprising separate, simultaneous or sequential administration of said antibiotic together with said alginate oligomer to said subject infected, suspected to be infected, or at risk of infection, with *Acinetobacter*.

4. The method of claim 1, said method comprising contacting a site and/or the *Acinetobacter* with said antibiotic together with said alginate oligomer.

5. The method of claim 1, wherein the antibiotic is selected from the group consisting of azithromycin, clarithromycin, dirithromycin, erythromycin, roxithromycin, telithromycin, CarbomycinA, josamycin, kitasamycin, midecamicine, oleandomycin, spiramycin, tylosin, troleandomycin, aztreonam, imipenem, meropenem, ertapenem, doripenem, panipenem/betamipron, biapenem, PZ-601, cefixime, cefdinir, cefditoren, cefoperazone, cefotaxime, cefpodoxime, ceftazidime, ceftibuten, ceftizoxime, ceftriaxone, cefepime, demeclocycline, doxycycline, minocycline, oxytetracycline, tetracycline, ciprofloxacin, enoxacin, gatifloxacin, levofloxacin, fomefloxacin, moxifloxacin, norfloxacin, ofloxacin, and trovafloxacin.

6. The method of claim 5 wherein the antibiotic is selected from the group consisting of ceftazidime, meropenem, aztreonam and ciprofloxacin.

7. The method of claim 1, wherein the antibiotic is a macrolide selected from the group consisting of azithromycin, clarithromycin, dirithromycin, erythromycin, roxithromycin and spiramycin.

8. The method of claim 1, wherein the *Acinetobacter* organism is *Acinetobacter baumannii* or *Acinetobacter Iwoffii*.

9. The method of claim 1, wherein the *Acinetobacter* organism is a clinical strain or a clinical isolate.

10. The method of claim 1, wherein the *Acinetobacter* organism is resistant to the antibiotic.

11. The method of claim 1, wherein the *Acinetobacter* organism is resistant to antibiotics in three or more of the classes macrolides, β-lactams, tetracyclines and quinolones.

12. The method of claim 1, wherein the alginate oligomer has an average molecular weight of less than 35,000 Daltons.

13. The method of claim 1, wherein the alginate oligomer has a number average degree of polymerization of 2 to 100.

14. The method of claim 1, wherein the alginate oligomer has up to 100 monomer residues.

15. The method of claim 1, wherein the alginate oligomer has at least 70% G residues.

16. The method of claim 15, wherein the alginate oligomer has at least 80% G residues.

17. The method of claim 15, wherein at least 80% of the G residues are arranged in G-blocks.

18. The method of claim 1, wherein the alginate oligomer has at least 70% M residues.

19. The method of claim 18 wherein the alginate oligomer has at least 80% M residues.

20. The method of claim 18, wherein at least 80% of the M residues are arranged in M blocks.

21. The method of claim 2, wherein the infection is:
(i) of an internal or external body surface selected from the group consisting of:
  (a) a surface in the oral cavity, the reproductive tract, the urinary tract, the respiratory tract, the gastrointestinal tract, the peritoneum, the middle ear, the prostate, vascular intima and the eye,
  (b) lung tissue, heart valves, skin, scalp, nails and the interior of wounds, and
  (c) the surface of adrenal, hepatic, renal, pancreatic, pituitary, thyroid, immune, ovarian, testicular, prostate, endometrial, ocular, mammary, adipose, epithelial, endothelial, neural, muscle, pulmonary, epidermis and osseous tissue; or
(ii) in a body fluid selected from the group consisting of blood, plasma, serum, cerebrospinal fluid, GI tract contents, sputum, pulmonary secretions and semen; or
(iii) in a body tissue selected from the group consisting of adrenal, hepatic, renal, pancreatic, pituitary, thyroid, immune, ovarian, testicular, prostate, endometrial, ocular, mammary, adipose, epithelial, endothelial, neural, muscle, pulmonary, epidermis and osseous tissue.

22. The method of claim 2, wherein the subject is selected from the group consisting of a subject with a pre-established infection, an immunocompromised subject, a subject undergoing intensive care, a subject undergoing critical care, a subject suffering from trauma, a subject with a burn, a subject with an acute wound, a subject with a chronic wound, a neonatal subject, an elderly subject, a subject with cancer, a subject suffering from an auto-immune condition, a subject with reduced epithelial secretion, a subject with reduced endothelial secretion, a subject with abrogated epithelial secretion, a subject with abrogated endothelial secretion, a subject with reduced epithelial secretion clearance, a subject with abrogated epithelial secretion clearance, a subject with reduced endothelial secretion clearance, a subject with abrogated endothelial secretion clearance and a subject fitted with a medical device.

23. The method of claim 22, wherein the subject is selected from the group consisting of a subject with a condition selected from HIV, sepsis, septic shock, AIDS, a cancer of the immune system, rheumatoid arthritis, diabetes mellitus type I, Crohn's disease, COPD, COAD, COAP, bronchitis, cystic fibrosis, emphysema, lung cancer, asthma, pneumonia and sinusitis, a subject preparing for chemotherapy, a subject undergoing chemotherapy, a subject recovering from chemotherapy a subject preparing for radiotherapy, a subject undergoing radiotherapy, a subject recovering from radiotherapy, an organ transplant subject, a subject resident in a healthcare institution and a smoker.

24. The method of claim 22, wherein the subject is a subject with a respiratory condition or disease.

25. The method of claim 1, wherein said *Acinetobacter* is on an animate or inanimate surface or in an animate or inanimate material.

26. The method of claim 1, wherein the *Acinetobacter* is on a surface selected from the group consisting of surfaces of food processing machinery, surfaces of food preparation machinery, surfaces of food storage machinery, surfaces of food dispensing machinery, surfaces of food processing equipment, surfaces of food preparation equipment, surfaces of food storage equipment, surfaces of food dispensing equipment, surfaces of drink processing machinery, surfaces of drink preparation machinery, surfaces of drink storage machinery, surfaces of drink dispensing machinery, surfaces of drink processing equipment, surfaces of drink preparing equipment, surfaces of drink storage equipment, surfaces of drink dispensing equipment, surfaces of air conditioning apparatus, surfaces of industrial machinery, surfaces of storage tanks, surfaces of medical equipment, surfaces of surgical equipment, surfaces of aquatic equipment, surfaces of marine equipment, surfaces of buildings and surfaces of other structures.

27. The method of claim 26 wherein the surface is selected from the group consisting of tanks, conveyors, floors, drains, coolers, freezers, equipment surfaces, walls, valves, belts, pipes, air conditioning conduits, cooling apparatus, food dispensing lines, drink dispensing lines, heat exchangers, boat hulls, dental waterlines, oil drilling conduits, contact lenses, contact lens storage cases, catheters, prosthetic devices and implantable medical devices.

28. The method of claim 1, wherein the *Aeinetobacter* is in a material selected from the group consisting of clinical waste, scientific waste, animal food stuffs, human food stuffs, personal hygiene products, cosmetics, drinking water supplies, waste water supplies, agricultural feedstuffs, agricultural water supplies, insecticide formulations, pesticide formulations, herbicide formulations, industrial lubricants, cell culture media, tissue culture media, cell cultures and tissue cultures.

29. The method of claim 13, wherein the alginate oligomer has a number average degree of polymerization of 2 to 35.

30. The method, of claim 14, wherein the alginate oligomer is a 2 to 35 mer.

31. The method of claim 24, wherein the respiratory condition or disease is selected from the group consisting of COPD, COAD, COAP, bronchitis, cystic fibrosis, emphysema, lung cancer, asthma, and pneumonia.

32. The method of claim 1, wherein the alginate oligomer has at least 85% G residues.

33. The method of claim 1, wherein the alginate oligomer has at least 90% G residues.

34. The method of claim 1, wherein the alginate oligomer has a number average degree of polymerization of 2 to 35.

35. The method of claim 1, wherein the alginate oligomer is a 3-35 mer.

36. The method of claim 1, wherein the alginate oligomer has a number average degree of polymerization of 5 to 35.

37. The method of claim 1, wherein the alginate oligomer is a 5-35 mer.

\* \* \* \* \*